United States Patent
Jauriqui

(10) Patent No.: US 9,927,403 B1
(45) Date of Patent: Mar. 27, 2018

(54) RESONANCE INSPECTION SORTING MODULE ARRAY

(71) Applicant: Vibrant Corporation, Albuquerque, NM (US)

(72) Inventor: Leanne Jauriqui, Albuquerque, NM (US)

(73) Assignee: Vibrant Corporation, Albuquerque, NM (US)

(*) Notice: Subject to any disclaimer, the term of this patent is extended or adjusted under 35 U.S.C. 154(b) by 436 days.

(21) Appl. No.: 14/697,945

(22) Filed: Apr. 28, 2015

Related U.S. Application Data

(60) Provisional application No. 61/985,014, filed on Apr. 28, 2014.

(51) Int. Cl.
*G01N 29/12* (2006.01)

(52) U.S. Cl.
CPC .................... *G01N 29/12* (2013.01)

(58) Field of Classification Search
CPC ..................... G01N 29/12; G01N 29/045
See application file for complete search history.

(56) References Cited

U.S. PATENT DOCUMENTS

| | | | |
|---|---|---|---|
| 5,408,880 A | 4/1995 | Rhodes et al. | |
| 5,425,272 A | 6/1995 | Rhodes et al. | |
| 5,495,763 A | 3/1996 | Rhodes et al. | |
| 5,631,423 A | 5/1997 | Rhodes | |
| 5,641,905 A | 6/1997 | Schwarz et al. | |
| 5,837,896 A | 11/1998 | Rhodes et al. | |
| 5,886,263 A | 3/1999 | Nath et al. | |
| 5,952,576 A | 9/1999 | Schwarz | |
| 5,965,817 A | 10/1999 | Schwarz et al. | |
| 5,992,234 A | 11/1999 | Rhodes et al. | |
| 6,199,431 B1 | 3/2001 | Nath et al. | |
| 8,744,983 B2 | 6/2014 | Miller | |

FOREIGN PATENT DOCUMENTS

WO 2011/062866 A1 5/2011

OTHER PUBLICATIONS

Schwarz et al., Process Compensated Resonant Testing in Manufacturing Process Control, Jul. 2005, Material Evaluation, pp. 736-739.*

* cited by examiner

*Primary Examiner* — Toan Le
(74) *Attorney, Agent, or Firm* — Marsh Fischmann & Breyfogle LLP

(57) ABSTRACT

A resonance inspection tool is disclosed that may be configured to assign a part to a first classification (accepted part) or a second classification (rejected part) using a cluster combination array. Such a cluster combination array may be defined from a first cluster array having a plurality of first clusters (each being of the first classification), and from a second cluster array having a plurality of second clusters (each being of the second classification). One cluster combination array presents all possible combinations of the same first cluster from the first cluster array and each second cluster from the second cluster array, where each such cluster combination includes a corresponding sort. Another cluster combination array presents all possible combinations of the same second cluster from the second cluster array and each first cluster from the first cluster array, where each such cluster combination includes a corresponding sort.

28 Claims, 14 Drawing Sheets

RESONANCE INSPECTION SORTING MODULE ARRAY

CROSS-REFERENCE TO RELATED APPLICATIONS

This patent application is a non-provisional of, and claims priority to, U.S. Provisional Patent Application Ser. No. 61/985,014, that is entitled "RESONANCE INSPECTION SORTING MODULE ARRAY," that was filed on Apr. 28, 2014, and the entire disclosure of which is hereby incorporated by reference in its entirety herein.

FIELD OF THE INVENTION

The present invention generally relates to the testing of parts and, more particularly, to a cluster-based resonance inspection of parts.

BACKGROUND OF THE INVENTION

A variety of techniques have been developed in which parts may be tested "nondestructively," meaning that the testing methodology enables defects to be identified without causing damage to the part. Examples of such nondestructive-testing methodologies include acoustic techniques, magnetic-particle techniques, liquid-penetrant techniques, radiographic techniques, eddy-current testing, and low-coherence interferometry, among others. There are various known advantages and disadvantages to each of these categories of testing methodologies, which are accordingly used in different environments.

Nondestructive-testing methods that use acoustic radiation generally operate in the ultrasonic range of the acoustic spectrum, and are valuable for a number of reasons. Such techniques are sensitive, for example, to both surface and subsurface discontinuities, enabling identification of defects both within the bulk and near the surface of a part. The depth of penetration for defect detection is generally superior to many other nondestructive-testing methodologies, and the techniques are highly accurate not only in determining the position of a defect, but also in estimating its size and shape.

SUMMARY

The present invention pertains to assessing a part using a plurality of clusters for purposes of assigning the part to a first classification (e.g., an accepted part classification) or to a second classification (e.g., a rejected part classification). A number of aspects of the present invention pertain to assessing a part using what may be characterized as a cluster combination array. Generally, such a cluster combination array may be defined by a certain cluster from one cluster array (one collection of clusters) and each cluster from another cluster array (a different collection of clusters). The individual clusters within each cluster array may be of a common classification. Other aspects of the present invention pertain to assessing a part against a plurality of clusters of a common classification.

A first aspect of the present invention is embodied by a method of evaluating a part. Part data is acquired on a first part and is ultimately used by a resonance inspection tool to assign the first part to a first classification or to a second classification, where this part data includes a frequency response of the first part. The resonance inspection tool includes a first cluster array and a second cluster array. The first cluster array is defined by a plurality of first clusters, where each first cluster is of a first classification (an accepted part classification), but where each first cluster is associated with a different resonance data pattern. The second cluster array is defined by a plurality of second clusters, where each second cluster is of a second classification (a rejected part classification), but where each second cluster is associated with a different resonance data pattern. The resonance inspection tool uses a fixed first cluster combination array to assess the first part. A particular fixed first cluster combination array includes a plurality of cluster combinations that is defined by the same first cluster from the first cluster array and each second cluster from the second cluster array. Therefore, the number of cluster combinations in a given fixed first cluster combination array will be the same as the number of second clusters that define the second cluster array. Each cluster combination of a particular fixed first cluster combination array has a dedicated sort.

The part data is tested against the sort for each cluster combination of a current fixed first cluster combination array that may be defined in accordance with the foregoing ("current" referring to the particular fixed first cluster combination array that is currently being used by the resonance inspection tool to assess the first part). If the sort for each cluster combination of the current fixed first cluster combination array provides a first classification sort result, the first part is assigned to the first classification. Otherwise, the part data is tested against the sort for each cluster combination of a different fixed first cluster combination array that may be defined in accordance with the foregoing (a "new" or "updated" current fixed first cluster combination array), and the foregoing is repeated. If the sort for at least one cluster combination of each fixed first cluster combination array (that may be defined from the first cluster array and the second cluster array, and that is assessed by the resonance inspection tool) provides a second classification sort result, the first part is assigned to the second classification.

A second aspect of the present invention is embodied by a method of evaluating a part. Part data is acquired on a first part and is ultimately used by a resonance inspection tool to assign the first part to a first classification or to a second classification, where this part data includes a frequency response of the first part. The resonance inspection tool includes a first cluster array and a second cluster array. The first cluster array is defined by a plurality of first clusters, where each first cluster is of a first classification (an accepted part classification), and where each first cluster is associated with a different resonance data pattern. The second cluster array is defined by a plurality of second clusters, where each second cluster is of a second classification (a rejected part classification), and where each second cluster is associated with a different resonance data pattern. The resonance inspection tool uses a fixed second cluster combination array to assess the first part. A particular fixed second cluster combination array includes a plurality of cluster combinations that is defined by the same second cluster from the second cluster array and each first cluster from the first cluster array. Therefore, the number of cluster combinations in a given fixed second cluster combination array will be the same as the number of first clusters that define the first cluster array. Each cluster combination of a particular fixed second cluster combination array has a dedicated sort.

The part data is tested against the sort for each cluster combination of a current fixed second cluster combination array that may be defined in accordance with the foregoing ("current" referring to the particular fixed second cluster combination array that is currently being used by the resonance inspection tool to assess the first part). If the sort for at least one cluster combination of the current fixed second cluster combination array provides a first classification sort result, the first part is assigned to the first classification. Otherwise, the part data is tested against the sort for each cluster combination of a different fixed second cluster combination array that may be defined in accordance with the foregoing (a "new" or "updated" current fixed second cluster combination array), and the foregoing is repeated. If the sort for each cluster combination of each fixed second cluster combination array (that may be defined from the first cluster array and the second cluster array, and that is assessed by the resonance inspection tool) provides a second classification sort result, the first part is assigned to the second classification.

A third aspect of the present invention is embodied by a method of evaluating a part. Part data is acquired on a first part and is ultimately used by a resonance inspection tool to assign the first part to a first classification or to a second classification, where this part data includes a frequency response of the first part. The resonance inspection tool includes a first cluster array and a second cluster array. The first cluster array is defined by a plurality of first clusters, where each first cluster is of a first classification (an accepted part classification), and where each first cluster is associated with a different resonance data pattern. The second cluster array is defined by a plurality of second clusters, where each second cluster is of a second classification (a rejected part classification), and where each second cluster is associated with a different resonance data pattern. User input to the resonance inspection tool may be used to select or identify (to the resonance inspection tool) a single one of the first clusters from the first cluster array. A fixed first cluster combination array used by the resonance inspection tool in accordance with the third aspect includes a plurality of cluster combinations that is defined by the selected first cluster from the first cluster array and each second cluster from the second cluster array. Therefore, the number of cluster combinations in the fixed first cluster combination array will be the same as the number of clusters that define the second cluster array. Each cluster combination of the fixed first cluster combination array has a dedicated sort in the case of the third aspect. The part data is tested against the sort for each cluster combination of the fixed first cluster combination array. If the sort for each cluster combination of the current fixed first cluster combination array provides a first classification sort result, the first part is assigned to the first classification. Otherwise, the first part is assigned to the second classification. Only one fixed first cluster combination array is used by the resonance inspection tool in the case of this third aspect.

A number of feature refinements and additional features are separately applicable to each of above-noted first, second, and third aspects of the present invention. These feature refinements and additional features may be used individually or in any combination in relation to each of the first, second, and third aspects.

The part data that is acquired on the first part may include at least resonance data or a frequency response of the first part to resonance testing by the resonance inspection tool. Such a frequency response may be in the form of a plot of a collection of responses of the first part at each frequency that may be used to drive the first part in a resonance inspection. For instance, if the first part is driven at frequency $f_1$, the amplitude of the response of the first part at this same frequency $f_1$ may be included in the noted plot at the frequency $f_1$; if the first part is driven at frequency $f_2$, the amplitude of the response of the first part at this same frequency $f_2$ may be included in the plot at the frequency $f_2$; if the first part is driven at frequency $f_3$, the amplitude of the response of the first part at this same frequency $f_3$ may be included in the plot at this frequency $f_3$; and so forth.

The first clustered parts within a particular first cluster of the first cluster array have a common resonance data pattern (but again where each of the first clusters have a different resonance data pattern; each first cluster may be characterized as having a unique resonance data pattern compared to all other first clusters and to all second clusters), and the second clustered parts within a particular second cluster of the second cluster array have a common resonance data pattern (but again where each of the second clusters have a different resonance data pattern; each second cluster may be characterized as having a unique resonance data pattern compared to all other second clusters and to all first clusters). Such a "common resonance data pattern" within a particular cluster may be over the entire range of drive frequencies that is used to generate the above-noted plot, or over a certain portion of this range of drive frequencies that is used to generate the above-noted plot.

The resonance inspection tool may be configured to test the part data against one or more sorts, and may determine whether the first part should be assigned to a first classification or a second classification based upon the relevant sort result(s). A "sort" may be characterized as an algorithm or a combination of algorithms that is used to determine if frequency-based criteria (i.e., one or more frequency-based criterion) exist in the frequency response of the first part. In one embodiment, the resonance inspection tool includes a signal generator (e.g., to excite the first part at one or more frequencies), one or more transducers (e.g., for transmitting a signal from the signal generator to the first part; for acquiring a frequency response from the first part), and a computer having at least one processor and cluster-based sort logic that is configured to test the part data against one or more sorts and to assign the first part to either the first classification or the second classification based upon the relevant sort result(s), all in accordance with the foregoing. The first cluster array, the second cluster array, each fixed first cluster combination array, and each fixed second cluster combination array, along with their corresponding sorts, may be incorporated by a non-transitory computer-readable storage medium that is incorporated by the resonance inspection tool.

Each first cluster of a first cluster array may include a plurality of first clustered parts that are each of the first classification and that exhibit a common resonance data pattern. Similarly, each second cluster of a second cluster array may include a plurality of second clustered parts that are each of the second classification and that exhibit a common resonance data pattern. Each first clustered part within each cluster of a first cluster array may be a non-defective part, while each second clustered part within each cluster of a second cluster array may be a defective part. All first clustered parts in each cluster of a first cluster array may have a common acceptance basis. All second clustered parts in each cluster of a second cluster array may have a common rejection basis (e.g., defect type, defect location, or both). There may be a different acceptance basis for each first cluster of a first cluster array. There may also be a different rejection basis for each second cluster of a second cluster array.

Parts may be clustered for purposes of a first cluster array based upon both being of a first classification and at least one first clustering parameter. Parts may be clustered for purposes of a second cluster array based upon both being of a second classification and at least one second clustering parameter. Parts for the first cluster array (first classification) and second cluster array (second cluster array) may be clustered on any appropriate basis, including based upon one or more clustering parameters. Each of the first clusters may include a plurality of first clustered parts, where each first clustered part in the same first cluster includes a common resonance data pattern. Each first clustered part in the same first cluster may also be associated with at least one of (i.e., in addition to having a common resonance data pattern): 1) a common manufacturer; 2) common component data; 3) common manufacturing data; and 4) common service-related data. Each of the second clusters may include a plurality of second clustered parts, where each second clustered part in the same second cluster includes a common resonance data pattern. Each second clustered part in the same second cluster may also include at least one of (i.e., in addition to having a common resonance data pattern): 1) a common manufacturer; 2) common component data; 3) common manufacturing data; and 4) common service-related data.

Based upon the foregoing: 1) a plurality of parts may be clustered into a plurality of first clusters based solely on a resonance data pattern basis; or 2) a plurality of parts may be clustered into a plurality of first clusters based on a common resonance data pattern basis in combination with at least one other clustering parameter such as a common manufacturer, common component data, common manufacturing data, and common service-related data. Based upon the foregoing: 1) a plurality of parts may be clustered into a plurality of second clusters based solely on a resonance data pattern basis; or 2) a plurality of parts may be clustered into a plurality of second clusters based on a common resonance data pattern basis in combination with at least one other clustering parameter such as a common manufacturer, common component data, common manufacturing data, and common service-related data. Although the same basic clustering parameter(s) may be used for each of the first and second clustering arrays (e.g., each first cluster could be defined by both a common resonance data pattern and a common manufacturer, and similarly each second cluster could be defined by both a common resonance data pattern and a common manufacturer), such need not be the case and as noted above (e.g., each first cluster could be defined by both a common resonance data pattern and a common manufacturer, while each second cluster could be defined by just a common resonance data pattern).

The resonance inspection tool may use cluster selection data in the assessment of the first part. For instance, cluster selection data that is received by the resonance inspection tool may be used to define a first cluster array that is used to define a fixed first cluster combination array (first aspect) or that is used to define a fixed second cluster combination array (second aspect). The cluster selection data may also be used in the selection of the single first cluster for purposes of the third aspect. In each instance, the cluster selection data may be at least one of: 1) manufacturer data; 2) component data; 3) manufacturing data; and/or 4) service-related data. In the case of the first and second aspects, the first cluster array that is used to define a cluster combination array may include multiple first clusters even when cluster selection data is provided to the resonance inspection tool (e.g., such that there are a corresponding number of fixed first cluster combination arrays in the case of the first aspect; such that each fixed second cluster combination array includes a corresponding number of cluster combinations in the case of the second aspect).

In the case where clusters are defined by a resonance data pattern and at least one other clustering parameter (i.e., where parts in each given cluster share a common resonance data pattern and also share at least one other common clustering parameter (e.g., a common manufacturer, common component data, common manufacturing data, common service-related data)), the data that is acquired on the first part may further include the corresponding clustering parameter(s) for use as the above-noted cluster selection data. Although clusters used by the resonance inspection tool could be defined by a resonance data pattern and at least one other clustering parameter, the first part could be assessed based solely on its resonance data or frequency response (although this option may not realize the benefits of this more advanced clustering).

A fourth aspect of the present invention is embodied by a method of evaluating a part. Part data is acquired on a first part and is ultimately used by a resonance inspection tool to assign the first part to a first classification (an accepted part classification) or to a second classification (a rejected part classification), where this part data includes a frequency response of the first part. The resonance inspection tool includes a plurality of clusters that each have a different resonance data pattern. Each of the clusters is defined by a plurality of clustered parts, all clustered parts in each cluster are of the second classification and have a common resonance data pattern, and each cluster has a different/dedicated sort. The part data is tested against the sort for each cluster. If the sort for each cluster provides a first classification sort result, the first part is assigned to the first classification. If the sort for at least one cluster provides a second classification sort result, the first part is assigned to the second classification.

A fifth aspect of the present invention is embodied by a method of evaluating a part. Part data is acquired on a first part and is ultimately used by a resonance inspection tool to assign the first part to a first classification (an accepted part classification) or to a second classification (a rejected part classification), where this part data includes a frequency response of the first part. The resonance inspection tool includes a plurality of clusters that each have a different resonance data pattern. Each of the clusters is defined by a plurality of clustered parts, all clustered parts in each cluster are of the first classification and have a common resonance data pattern, and each cluster has a different/dedicated sort. The part data is tested against the sort for each cluster. If the sort for at least one cluster provides a first classification sort result, the first part is assigned to the first classification. If the sort for each cluster provides a second classification sort result, the first part is assigned to the second classification.

A sixth aspect of the present invention is embodied by a method of evaluating a part. Part data is acquired on a first part and is ultimately used by a resonance inspection tool to assign the first part to a first classification (an accepted part classification) or to a second classification (a rejected part classification), where this part data includes a frequency response of the first part. The resonance inspection tool includes a plurality of clusters that each have a different resonance data pattern. Each of the clusters is defined by a plurality of clustered parts, all clustered parts in each cluster are of the first classification and have a common resonance data pattern, and each cluster has a different/dedicated sort. The part data is tested against the sort for a given cluster. If the sort for this cluster provides a first classification sort result, the first part is assigned to the first classification. Otherwise, the part data is tested against the sort of another cluster until a given sort provides a first classification sort result or until the part data has been tested against the sort for all clusters. If the sort for each cluster provides a second classification sort result (i.e., the part data has been tested against the sort for each cluster, and none of these sorts yielded a first classification sort result), the first part is assigned to the second classification.

A number of feature refinements and additional features are separately applicable to each of above-noted fourth, fifth, and sixth aspects of the present invention. These feature refinements and additional features may be used individually or in any combination in relation to each of the fourth, fifth, and sixth aspects. The acquisition of part data and the sorts referenced in relation to the fourth, fifth, and sixth aspects may be in accordance with the first, second, and third aspects. Each clustered part within a particular cluster for purposes of each of the fourth, fifth, and sixth aspects have a common resonance data pattern in accordance with the meaning set forth above in relation to the first, second, and third aspects.

Parts may be clustered for purposes of the fourth, fifth, and sixth aspects based upon at least a common resonance data pattern (e.g., parts in each given cluster share a common resonance data pattern). Parts may be clustered for purposes of the fourth, fifth, and sixth aspects based upon a common resonance data pattern and at least one other clustering parameter (e.g., parts in each given cluster may share a common resonance data pattern and may also share at least one other common clustering parameter). Those corresponding features that are addressed above therefore may be used by each of the fourth, fifth, and sixth aspects as well.

A number of feature refinements and additional features are separately applicable to each of above-noted aspects of the present invention. These feature refinements and additional features may be used individually or in any combination in relation to each of the above-noted aspects of the present invention.

The various aspects of the present invention each may be implemented as a method and/or as a resonance inspection system or tool. A resonance inspection of a part-under-test may include exciting a part-under-test at a plurality of input frequencies and obtaining a frequency response of the part-under-test (e.g., to acquire/assess resonance data). A resonance inspection may be characterized as obtaining a whole body frequency response of the part-under-test using a number of different drive or input frequencies. In any case, the frequency response from the inspection of a part-under-test may be tested against the sort of one or more clusters or the sort of one or more cluster combinations, as the case may be and in accordance with any of the foregoing aspects. As noted, each cluster array and each cluster combination array, along with their corresponding sorts, may be incorporated by a non-transitory computer-readable storage medium that is in turn incorporated/utilized by the resonance inspection tool. In the case of a resonance inspection system or tool, an assessment module may utilize cluster-based sort logic and which may be configured to execute the assessments noted herein, and the part-under-test may be excited and the frequency response may be obtained in accordance with any one or more of the following configurations.

A resonance inspection of a part-under-test in accordance with the present invention may utilize a first transducer that excites or drives the part-under-test at multiple frequencies (e.g., by sweeping through a predetermined range of frequencies in any appropriate manner), along with at least one other transducer that measures the frequency response of this part-under-test to such excitations or drive frequencies (e.g., thereby encompassing using two "receiver" transducers). Any number of frequencies may be used to excite the part-under-test for the inspection, and the excitation frequencies may be input to the part-under-test in any appropriate pattern and for any appropriate duration. Another option is to use a single transducer for performing an inspection of the part-under-test. In this case, a transducer may drive the part-under-test at a certain frequency for a certain amount of time, and thereafter this same transducer may be used to obtain the frequency response of the part-under-test (e.g., after terminating the driving of the transducer at an input frequency). This may be repeated for multiple input or drive frequencies.

Any appropriate combination of excitation or drive frequencies may be used for an inspection in accordance with the present invention. Each transducer that is used to perform an inspection may be of any appropriate size, shape, configuration, and/or type. Although an inspection in accordance with the present invention could possibly be performed in situ (e.g., with the part in an installed condition or state), such an inspection will more typically be performed prior to installing a part for its end-use application or with the part being in an uninstalled condition or state.

A resonance inspection of a part-under-test in accordance with the present invention may include using at least one transducer that excites the part-under-test through a range of frequencies, and using at least two other transducers to measure the frequency response of the part-under-test. Another option for an inspection of the part-under-test is to use a first transducer that excites the part-under-test at a number of different frequencies, and using this same transducer to measure the frequency response of the part-under-test.

A resonance inspection of a part-under-test in accordance in accordance with the present invention may include exciting the part-under-test using at least one drive transducer that is in contact with the part-under-test. Another option for an inspection is to excite the part-under-test using at least one drive transducer that is maintained in spaced relation to the part-under-test throughout the inspection. In one embodiment, such a drive transducer (e.g., a drive transducer that is spaced from the part-under-test for the inspection) may be in the form of a laser.

A resonance inspection of a part-under-test in accordance with the present invention may entail obtaining a frequency response of this part using at least one receive transducer that is in contact with the part-under-test. Another option for this inspection is to obtain a frequency response of the part-under-test using at least one receive transducer that is maintained in spaced relation to this part-under-test. In one embodiment, a receive transducer used in the inspection of the part-under-test is in the form of a laser. The inspection of the part-under-test may include obtaining a frequency response of this part-under-test using laser vibrometry. The frequency response of the part-under-test in this case may be obtained from a single location using laser vibrometry. Another option for this case is to obtain the frequency response of the part-under-test by laser scanning multiple locations on the surface of this part-under-test.

Any feature of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a resonance inspection system/tool utilizes "a frequency response transducer" alone does not mean that the resonance inspection system/tool utilizes only a single frequency response transducer). Moreover, any failure to use phrases such as "at least one" also does not limit the corresponding feature to the singular (e.g., indicating that a resonance inspection system/tool utilizes "a frequency response transducer" alone does not mean that the resonance inspection system/tool utilizes only a single frequency response transducer). Use of the phrase "at least generally" or the like in relation to a particular feature encompasses the corresponding characteristic and insubstantial variations thereof (e.g., indicating that a structure is at least generally cylindrical encompasses the structure being cylindrical). Finally, a reference of a feature in conjunction with the phrase "in one embodiment" does not limit the use of the feature to a single embodiment.

DETAILED DESCRIPTION

Various applications of resonance inspection (e.g., resonance ultrasound spectroscopy; process compensated resonance testing) are addressed herein. Various principles that may relate to resonance inspection are addressed in the following U.S. patents, the entire disclosures of which are incorporated by reference in their entirety herein: U.S. Pat. Nos. 5,408,880; 5,425,272; 5,495,763; 5,631,423; 5,641,905; 5,837,896; 5,866,263; 5,952,576; 5,965,817; 5,992,234; and 6,199,431.

Figure 1:
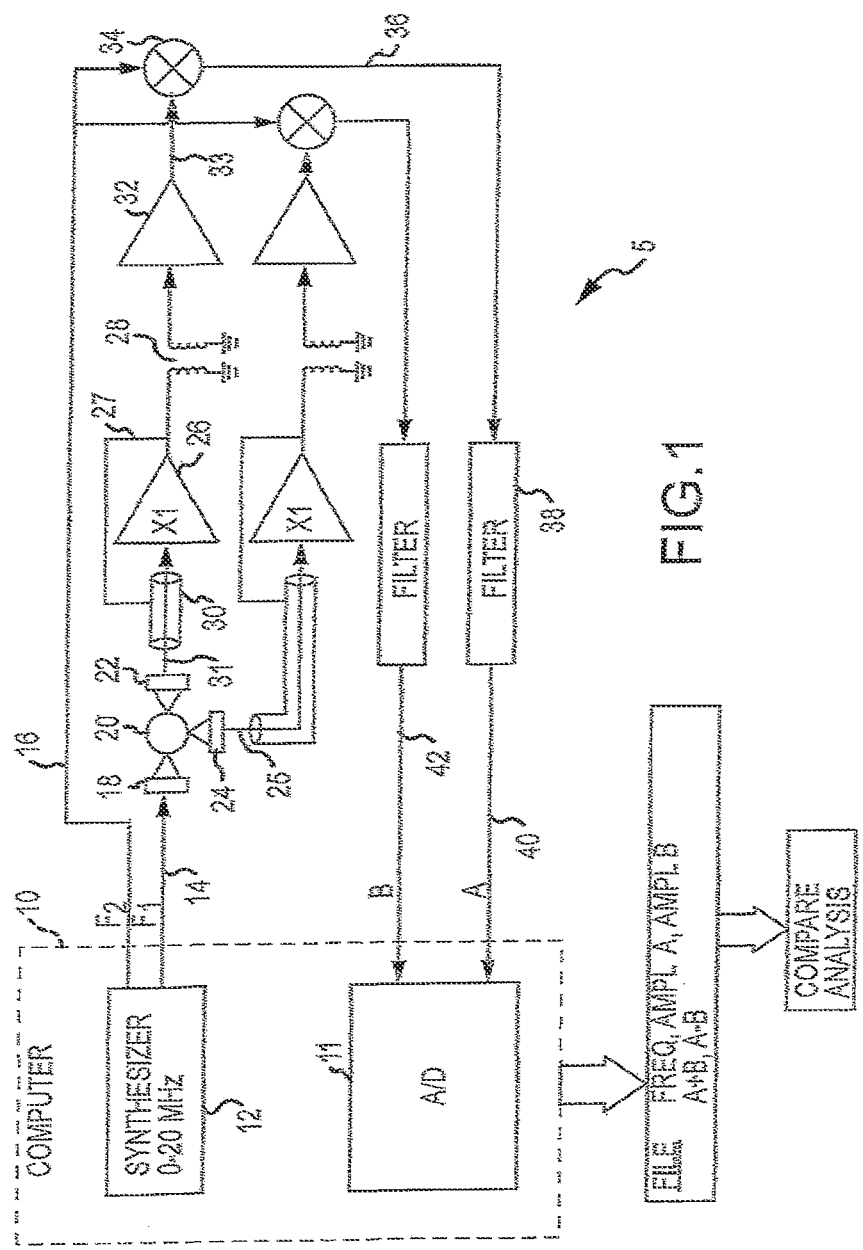
FIG. 1 is a block-diagram of one embodiment of a resonance inspection tool.
Figure 2:
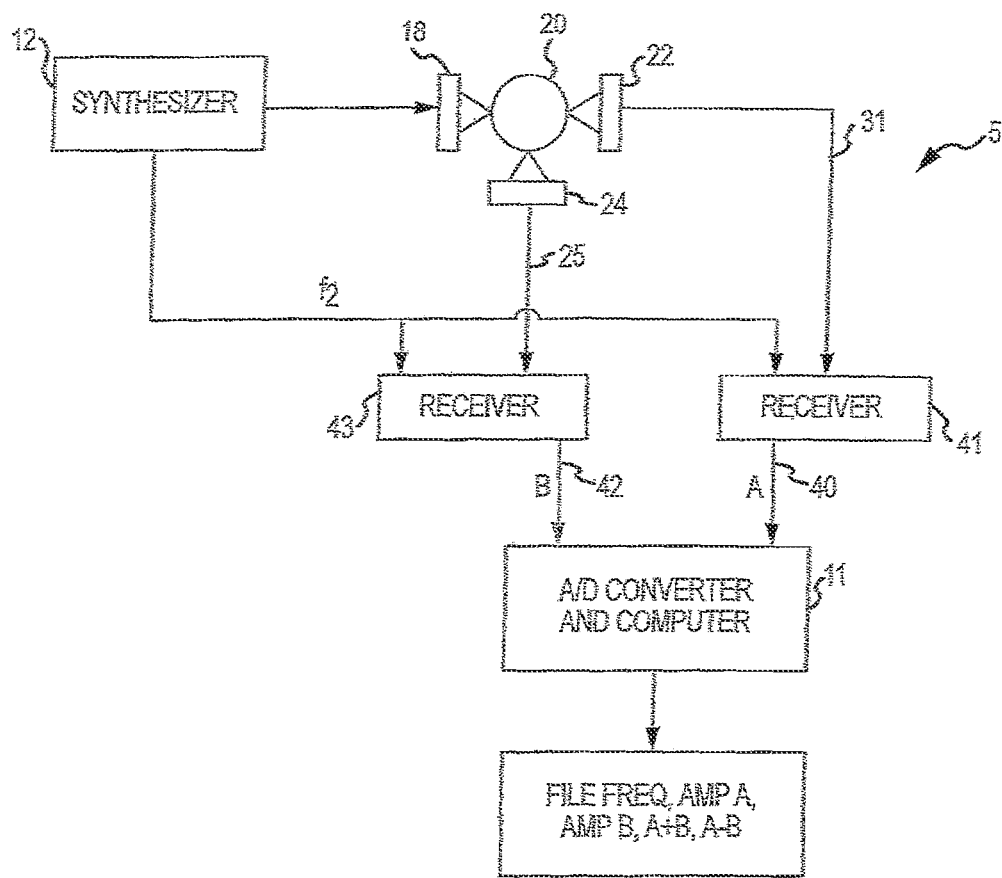
FIG. 2 shows a simplified block diagram of the resonance inspection tool of FIG. 1.

One embodiment of a resonance inspection tool or system (e.g., for accommodating resonant ultrasound spectroscopy measurement with a plurality of sensors; for process compensated resonance testing) is illustrated in FIGS. 1 and 2, and is identified by reference numeral 5. The resonance inspection tool 5 includes a computer 10 that provides for control of a synthesizer 12 and an analog to digital converter 11 for each data input channel connected to each receiving or response transducer 22, 24 of the resonance inspection tool 5. Transducer 22 has an output on line 31, while transducer 24 has an output on line 25.

Synthesizer 12 may have a frequency range from greater than 0 to 20 M Hertz. Other frequency ranges may be appropriate. Synthesizer 12 provides two outputs which are the frequency F1 at output 14 and a second output which is the frequency F2 at line 16. In one embodiment, the frequency F2 is either F1 plus a constant frequency such as 1000 Hertz for heterodyne operation of the receiver, or at F1 for homodyne operation. A first transducer 18 (e.g., the input or driving transducer) is excited at a frequency F1 by synthesizer 12. Transducer 18 provides vibration (e.g., ultrasonic) to an object 20 to be tested via resonance inspection.

The response of the object 20 is then received by two separate output transducers 22 and 24. The circuitry from the output transducer 22 and A/D converter 11 can be identical to circuitry between output transducer 24 and A/D converter 11. For this reason, only the circuitry between output transducer 22 and A/D converter 11 will be discussed below. The times one (.times.1) amplifier 26 is connected to the output transducer 22, provides current for transformer 28, and has a feedback 27.

The output of transducer 22 is connected to a receiver 41 (FIG. 2). Receiver 41 is used for the purpose of providing amplification and noise rejection in the circuit between output transducer 22 and A/D converter 11. The output A (line 40) is applied to the A/D converter 11 within the computer 10. The A/D converter 11 provides an A/D conversion for each of lines 40 and 42. The converted information is then entered into a file which consists of the measured frequency, the amplitude of A, the amplitude of B, the amplitude of A plus B, and the amplitude of A minus B. This file is then used for further analysis of the spectrum to determine characteristics of a part 20 being tested.

The times one (.times.1) amplifier 26 provides feedback to an inner coaxial cable shield 30 which surround the lead from transducer 22 to amplifier 26. Shield 30 is another grounded shield which can also be used for noise suppression. The outer surrounding coaxial cable is not shown in FIG. 1. If lead 31 is short, the shield 30 may be omitted because capacitance will not be too large. The purpose of the inner shield 30 is to provide a cancellation of capacitance of the lead 31.

The transformer 28 may be a 4:1 step-down transformer used for impedance matching to the input of amplifier 32. In this regard, it should be noted that the output impedance of amplifier 26 may be much lower than the output impedance of transducer 22. This provides for the power gain and the necessary feedback to shield 30. The amplifier 32 may have a gain factor of 100:1 or a 40 db gain. Other gain factors may be appropriate. The amplifier 26 may be a broad-band amplifier having a band pass on the order of 50 M Hertz.

Mixer 34 has an output signal (e.g., a 1 K Hertz signal) having a magnitude which is proportional to the magnitude of the frequency F1 provided on line 14 from synthesizer 12. The function of the synthesizer 12 is to provide a point-by-point multiplication of instantaneous values of inputs on lines 16 and 33. The mixer 34 also has many high frequency output components which are of no interest. The high frequency components are therefore filtered out by the low-band pass filter 38 which is connected to mixer 34 by line 36. Filter 38 serves to clean-up the signal from mixer 34 and provide a voltage on line 40 which is only the output signal at an amplitude which is proportional to the amplitude of the output 31 of transducer 22.

Operation of the resonance inspection tool 5 will be briefly described in relation to measurement steps performed by measurement of the output of either transducer 22 or transducer 24 controlled by computer 10. A measurement cycle may be initiated, and provides initialization for the frequency F and the desired frequency step. The frequency step may be 1 Hertz or any other frequency selected for the measurement. Although a constant frequency step may be utilized, the frequency step may be determined by any appropriate algorithm. In one embodiment, the frequency step is determined by determining the start frequency and the stop frequency, and dividing the frequency difference by the number of steps desired for the measurement. In any case, the synthesizer 12 is configured to provide a plurality of input or drive frequencies to transducer 18.

Once a signal is picked up by the receiver (i.e., an output on line 33), a pause for ring delay there is a provided. The pause for ring delay may be on the order of 30 milliseconds, although other ring delays can be used if the object under test 20 has resonances that are narrower than a few Hertz. The purpose of the pause is to give the object 20 an opportunity to reach its steady state magnitude in response to a steady input from transducer 18. The pause time is time after the frequency is applied and before detection is initiated.

After the ring delay is complete, analog-to-digital converter 11 provides an output that can be used by the data recording computer. The output of the A/D conversion is then written to a file by the computer 10 for the purpose of analysis of the data by another program. Data comprising the unique signature or characterizing of the object 20 is written into file as it is created. Reading may be stopped when a read frequency is present and step 66 stops the program. Once information is entered into file, subsequent processing can be used to generate a signature or characterize the object 20 such as the resonant magnitudes, the sum of resonant magnitudes, the difference of resonant magnitudes, or other manipulations of the multiple channel multiple frequency measurement which is used to perform the unique signature of the object 20. The magnitude of the outputs at each sensor location for each resonance frequency may be compared.

Figure 3:
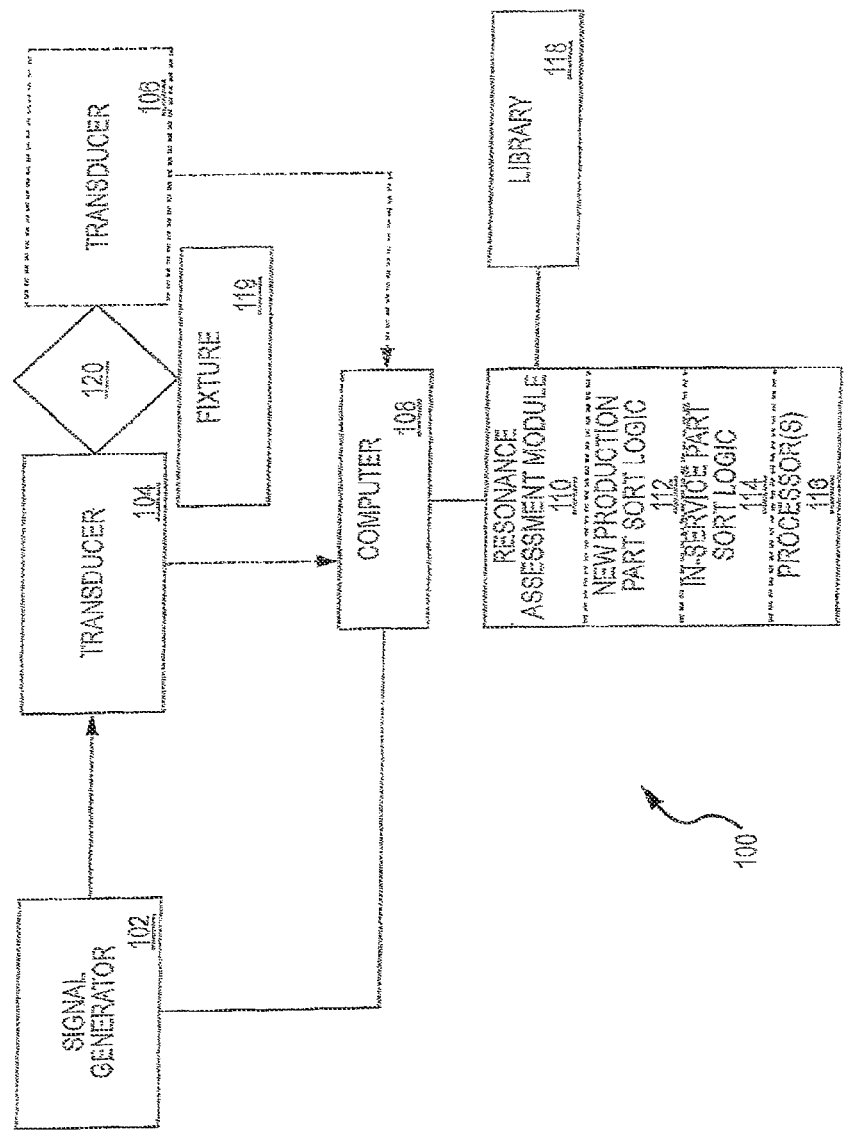
FIG. 3 is a block-diagram of another embodiment of a resonance inspection tool.

Another embodiment of a resonance inspection tool or system is illustrated in FIG. 3 and is identified by reference numeral 100. The resonance inspection tool 100 may be used to assess a part or part-under-test 120. This part 120 may be retained in a fixture 119 in any appropriate manner for execution of a resonance inspection.

The resonance inspection tool 100 includes a signal generator 102 of any appropriate type, at least one transducer (e.g., transducer 104), and a computer 108. The transducer 104 may be of any appropriate type. In one embodiment, the transducer 104 is in physical contact with the part 120 throughout execution of the inspection of the part 120, and in this case may be characterized as being part of the fixture 119 for the part 120. Another embodiment has the transducer 104 being maintained in spaced relation to the part 120 throughout execution of the resonance inspection of the part 120 (e.g., a laser, such as Nd:YAG lasers, TEA $CO_2$ lasers, excimer lasers, or diode lasers).

The computer 108 may include what may be characterized as a resonance assessment module 110 (e.g., incorporated/embodied by a non-transitory computer-readable storage medium). Generally, the resonance assessment module 110 may be configured to evaluate the results of a resonance inspection, for instance for purposes of determining whether the part 120 should be accepted or rejected by the resonance inspection tool 100, determining whether the part 120 is at an end-of-life state or condition, or the like. A part 120 that is "accepted" by the resonance inspection tool 100 may mean that the resonance inspection tool 100 has determined that the part 120 may be put into service (e.g., utilized for its intended purpose(s) and/or used according to its design specifications). In one embodiment, a part 120 that has been accepted by the resonance inspection tool 100 means that the tool 100 has determined that the part 120 is free of defects, is not in an end-of-life condition or state, is aging normally, or any combination thereof. A part 120 that is "rejected" by the resonance inspection tool 100 may mean that the resonance inspection tool 100 has determined that the part 120 should not be put into service (e.g., should not be utilized for its intended purpose(s) and/or should no longer be used according to its design specifications). In one embodiment, a part 120 that has been rejected by the resonance inspection tool 100 means that the tool 100 has determined that the part 120 includes at least one defect, is at or near an end-of-life condition or state, is aging abnormally, or any combination thereof.

A part 120 that is analyzed or assessed by the resonance inspection tool 100 may be of any appropriate size, shape, configuration, type, and/or class. For purposes of the resonance inspection tool 100, there could be two part classes. One part class includes new production parts—newly manufactured parts that have not yet been released from production (e.g., parts that have not been shipped for use by an end user or customer). New production parts include parts that may have undergone at least some post-production testing of any appropriate type (including without limitation a resonance inspection). Another part class includes in-service parts—parts that have been released from production for use in one or more end-use applications. An "in-service part" in the context of the embodiments to be addressed herein encompasses a part that has been used to at least some extent after having been released by the manufacturer. An in-service part may be a part that has been put into use by a party other than the manufacturer (e.g., a customer or end user). Although an in-service part could be used autonomously or independently of any other parts, an in-service part also may be incorporated by an assembly or system (e.g., a turbine blade (an in-service part) in a jet engine (an assembly or system)).

The signal generator 102 generates signals that are directed to the transducer 104 for transmission to the part 120 in any appropriate manner/fashion (e.g., via physical contact between the transducer 104 and the part 120; through a space between the transducer 104 and the part 120). Signals provided to the transducer 104 by the signal generator 102 are used to mechanically excite the part 120 (e.g., to provide energy to the part 120 for purposes of inducing vibration). Multiple frequencies may be input to the part 120 through the transducer 104 in any appropriate manner. This may be characterized as "sweeping" through a range of frequencies that are each input to the part 120, and this may be done in any appropriate manner for purposes of the resonance inspection tool 100. Any appropriate number/range of frequencies may be utilized, and any appropriate way of progressing through a plurality of frequencies (e.g., a frequency range) may be utilized by the resonance inspection tool 100.

In one embodiment, at least one other transducer 106 is utilized in the resonance inspection of the part 120 using the resonance inspection tool 100 of FIG. 3, including where two transducers 106 are utilized (e.g., in accordance with the embodiment of FIGS. 1 and 2 noted above). Each of the transducers 106, as well as the input or drive transducer 104, may be in physical contact with the part 120. It may be such that the part 120 is in fact entirely supported by the transducer 104 and any additional transducers 106 (e.g., the drive transducer 104 and one or more receive transducers 106 may define the fixture 119). Each transducer 106 that is utilized by the resonance inspection tool 100 is used to acquire the frequency response of the part 120 to the frequencies input to the part 120 by the drive transducer 104, and therefore each transducer 106 may be characterized as an output or receiver transducer 106.

One or more transducers 106 utilized by the resonance inspection tool 100 may be maintained in physical contact with the part 120 throughout the resonance inspection. Another option is for one or more of the transducers 106 to be maintained in spaced relation with the part 120 throughout the resonance inspection. A transducer 106 in the form of a laser may be maintained in spaced relation with the part 120 throughout the resonance inspection, and may be utilized to obtain the frequency response of the part 120. Representative lasers that may be utilized as a transducer 106 by the resonance inspection system 100 include without limitation Nd:YAG lasers, TEA $CO_2$ lasers, excimer lasers, or diode lasers. In one embodiment, the frequency response of the part 120 is acquired by laser vibrometry utilizing at least one transducer 106. A given transducer 106 in the form of a laser may acquire resonance data on the part 120 from a single location, or a given transducer 106 in the form of a laser could acquire resonance data on the part 120 by scanning the laser over multiple locations on the part 120.

Another embodiment of the resonance inspection tool 100 of FIG. 3 utilizes only the transducer 104. That is, no additional transducers 106 are utilized by the resonance inspection tool 100 in this case, and therefore the transducer 106 is presented by dashed lines in FIG. 3. In this case, the transducer 104 is used to input a drive signal to the part 120 (e.g., to excite the part 120 at a plurality of different frequencies), and is also used to acquire the frequency response of the part 120 to these input drive frequencies. Representative configurations for this drive/receive transducer configuration 104 include without limitation piezoceramic, piezocomposites, piezoelectric quartz crystal, and other electromechanical materials.

In the above-noted drive/receive transducer configuration 106, a first drive signal at a first frequency (from the signal generator 102) may be transmitted to the part 120 through the transducer 104, the transmission of this first drive signal may be terminated, and the transducer 104 may be used to acquire a first frequency response of the part 120 to this first drive signal (including while a drive signal is being transmitted to the part 120). The signal generator 102 may also be used provide a second drive signal at a second frequency to the transducer 104, which in turn transmits the second drive signal to the part 120, the transmission of this second drive signal may be terminated, and the transducer 104 may once again be used to acquire a second frequency response of the part 120 to this second drive signal (including while a drive signal is being transmitted to the part 120). This may be repeated any appropriate number of times and utilizing any appropriate number of frequencies and frequency values. One or more drive signals may be sequentially transmitted to the part 120 by the signal generator 102 and transducer 104, one or more drive signals may be simultaneously transmitted to the part 120 by the signal generator 102 and transducer 104, or any combination thereof.

The frequency response of the part 120 is transmitted to the computer 108 of the resonance inspection tool 100 of FIG. 3. This computer 108 may be of any appropriate type and/or configuration, and is used by the resonance inspection tool 100 to evaluate the part 120 in at least some fashion (e.g., to determine whether to accept or reject the part 120). Generally, the part 120 is vibrated by the transducer 104 according to a predetermined signal(s), and the part 120 is evaluated by the resulting vibrational (e.g., whole body) response of the part 120. For instance, this evaluation may entail assessing the part 120 for one or more defects of various types, assessing whether the part 120 is at or near the end of its useful, life, assessing whether the part 120 is aging normally or abnormally, or any combination thereof.

The computer 108 may incorporate and utilize the above-noted resonance assessment module 110 to evaluate the response of the part 120 to a resonance inspection. The resonance assessment module 110 may be of any appropriate configuration and may be implemented in any appropriate manner. In one embodiment, the resonance assessment module 110 includes at least one new production part sort logic 112 (e.g., logic configured to determine whether to accept or reject new production parts), at least one in-service part sort logic 114 (e.g., logic configured to determine whether to accept or reject in-service parts), along with one or more processors 116 of any appropriate type and which may be implemented in any appropriate processing architecture. The assessment of the response of the part 120 to the input drive signals may entail comparing the response to a library 118 utilized by the resonance inspection tool 100. This library 118 may be stored on a computer-readable storage medium of any appropriate type or types and in a non-transitory form (e.g., a non-transitory computer-readable storage medium), including without limitation by using one or more data storage devices of any appropriate type and utilizing any appropriate data storage architecture.

Figure 4:
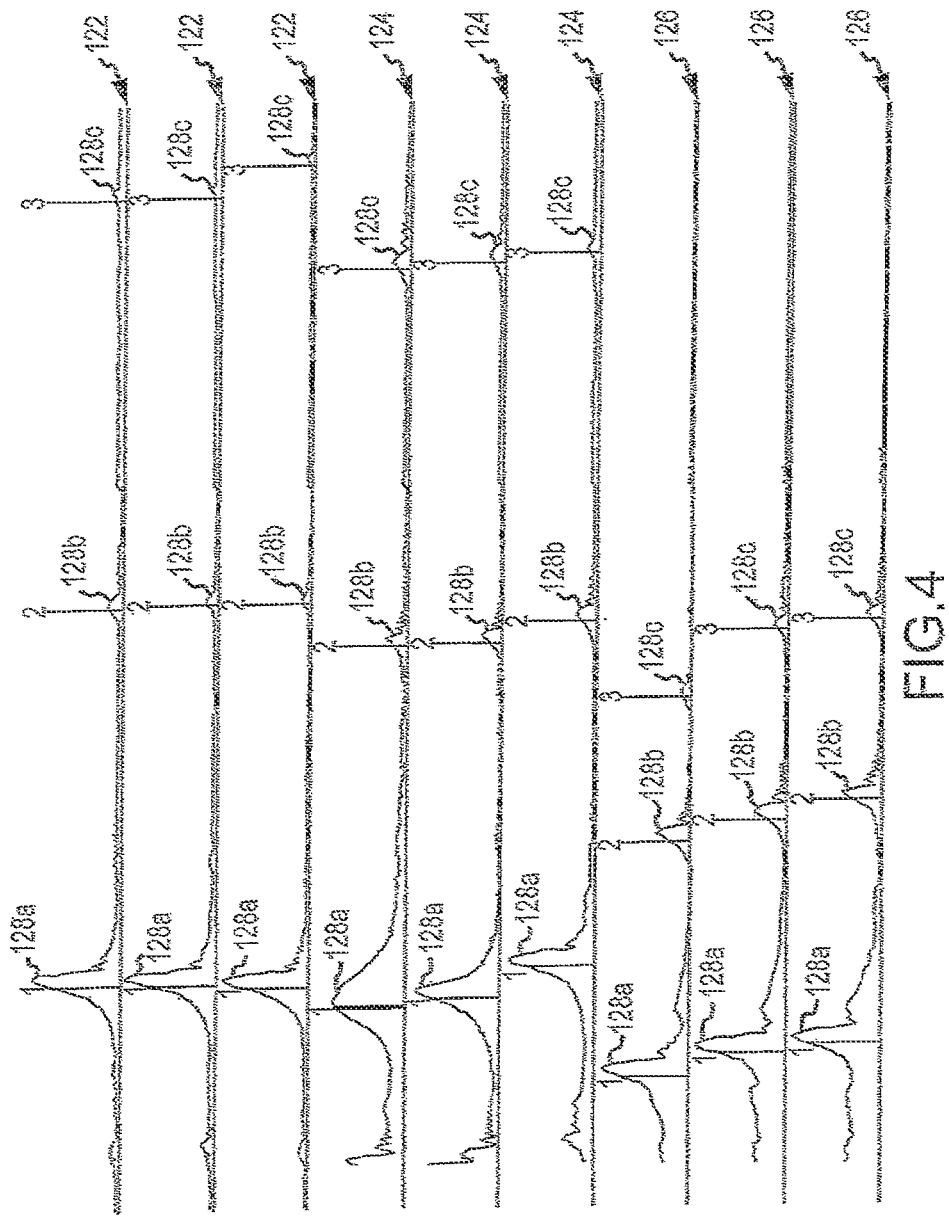
FIG. 4 presents various resonance inspection results of parts that may be included in the library utilized by the resonance inspection tool of FIG. 3.

The library 118 of the resonance inspection tool 100 may include various types of resonance inspection results to allow the resonance inspection tool 100 to assess a part 120. Generally, the resonance inspection results from the part 120 are compared with data in the library 118 from at least one other part that is the same as the part 120 in one or more respects (e.g., a part 120 in the form of a turbine blade will be compared to turbine blade data in the library 118; a part 120 in the form of a turbine blade will not be compared with ball bearing data in the library 118). Representative resonance inspection results are presented in FIG. 4, and are of a type that may be included in the library 118. The three spectra 122 shown in FIG. 4 represent the frequency response of a new production part 120 to a certain input frequency, and where this new production part 120 has been accepted by the resonance inspection tool 100. Note how the three peaks 128a, 128b, and 128c differ in at least one respect between the various spectra 122, but yet the corresponding new production part 120 is acceptable in all three instances.

The three spectra 124 shown in FIG. 4 represent the frequency response of an in-service part 120 to a certain input frequency, and where this in-service part 120 has been accepted by the resonance inspection tool 100. Note how the three peaks 128a, 128b, and 128c in the spectra 124 differ in at least one respect from the corresponding peaks 128a, 128b, and 128c in the spectra 122 (again, associated with a new production part 120).

The three spectra 126 shown in FIG. 4 represent the frequency response of an in-service part 120 to a certain input frequency, and where this in-service part 120 has been rejected by the resonance inspection tool 100. Note how the three peaks 128a, 128b, and 128c in the spectra 126 differ in at least one respect from the corresponding peaks 128a, 128b, and 128c in the spectra 124 (again, associated with an in-service part 120 that the resonance inspection tool 100 would accept). Generally, each of the peaks 128a, 128b, and 128c in the spectra 126 has shifted to the left compared to the corresponding peaks 128a, 128b, and 128c in the spectra 122 and 124. Moreover, note the "compression" between the peaks 128a, 128b in the spectra 126 compared to the spectra 122, 124, as well as the "compression" between the peaks 128b, 128c in the spectra 126 compared to the spectra 122, 124.

Figure 5:
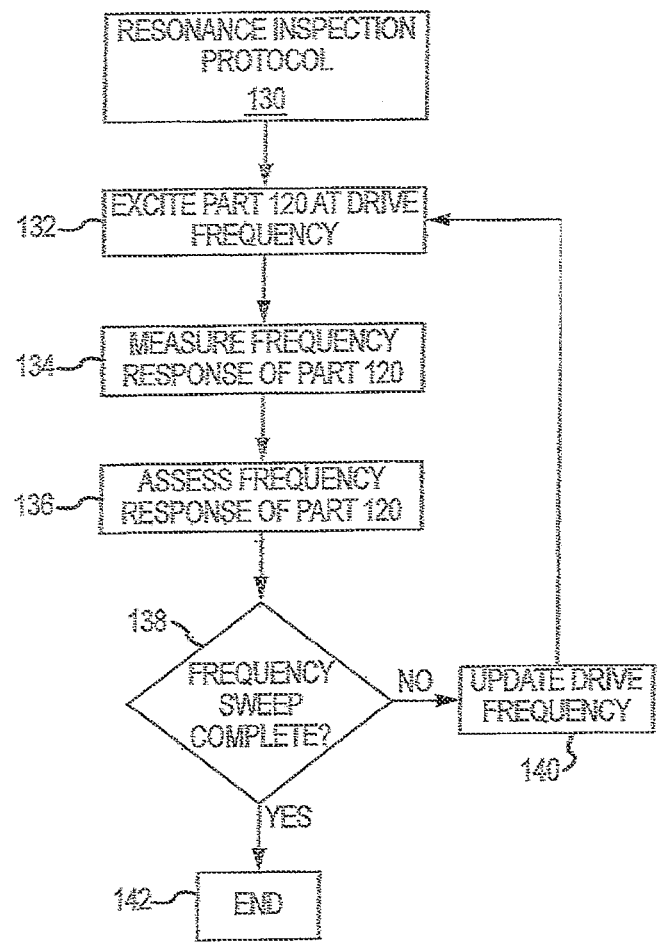
FIG. 5 is one embodiment of a resonance inspection protocol that may be utilized by a resonance inspection tool.

One embodiment of a resonance inspection protocol that may be utilized by the resonance inspection tool 100 of FIG. 3 is presented in FIG. 5 and is identified by reference numeral 130. Step 132 of the resonance inspection protocol 130 is directed to exciting a part 120 at a drive frequency (e.g. via a signal from the signal generator 102 that is input to the part 120 through the transducer 104). The response of the part 120 is obtained or measured pursuant to step 134 (e.g., via one or more transducers 106; via the transducer 104 in a single transducer configuration). It should be appreciated that steps 132 and 134 may be executed in at least partially overlapping relation (e.g., the frequency response of the part 120 could be obtained as a drive signal is being applied to the part 120), although steps 132 and 134 could be sequentially executed as well.

The frequency response of the part 120 is assessed pursuant to step 136 of the resonance inspection protocol 130. Step 138 of the protocol 130 is directed to determining if the frequency sweep is complete—whether each of the desired drive frequencies has been input to the part 120. If not, the protocol 130 proceeds to step 140, and which is directed to updating or changing the drive frequency to be input to the part 120. Control is then returned to step 132 of the protocol 130 for repetition in accordance with the foregoing. Once the part 120 has been driven at each of the desired frequencies, the protocol 130 may be terminated pursuant to step 142.

Step 136 of the resonance inspection protocol 130 is again directed to assessing the response (e.g., frequency; whole body) of the part 120 (e.g., using the sort logic 112 or 114 and/or comparing the response of the part 120 to the library 118 of the resonance inspection tool 100). This assessment may be undertaken at any appropriate time and in any appropriate manner. For instance, the assessment associated with step 136 could be undertaken while the part 120 continues to be driven by a signal at one or more frequencies. Another option is for the assessment provided by step 136 to be undertaken only after all drive signals have been input to the part 120 (step 132), after the all frequency responses have been obtained (step 134), or both.

A frequency response for a part, as described herein and including for purposes of step 136 of the resonance inspection protocol 130 of FIG. 5, may actually be in the form of a plot or compilation of a collection of responses of a part-under-test (e.g., part 120) at each frequency that may be used to drive the part-under-test. For instance, if a part-under-test is driven at frequency $f_1$, the amplitude of the response of the part-under-test at this same frequency $f_1$ may be included in the noted plot at the frequency $f_1$; if the part-under-test is driven at frequency $f_2$, the amplitude of the response of the part-under-test at this same frequency $f_2$ may be included in the plot at the frequency $f_2$; if the part-under-test is driven at frequency $f_3$, the amplitude of the response of the part-under-test at this same frequency $f_3$ may be included in the plot at this frequency $f_3$; and so forth. Any such plot is within the scope of a "frequency response" as set forth herein.

Figure 6:
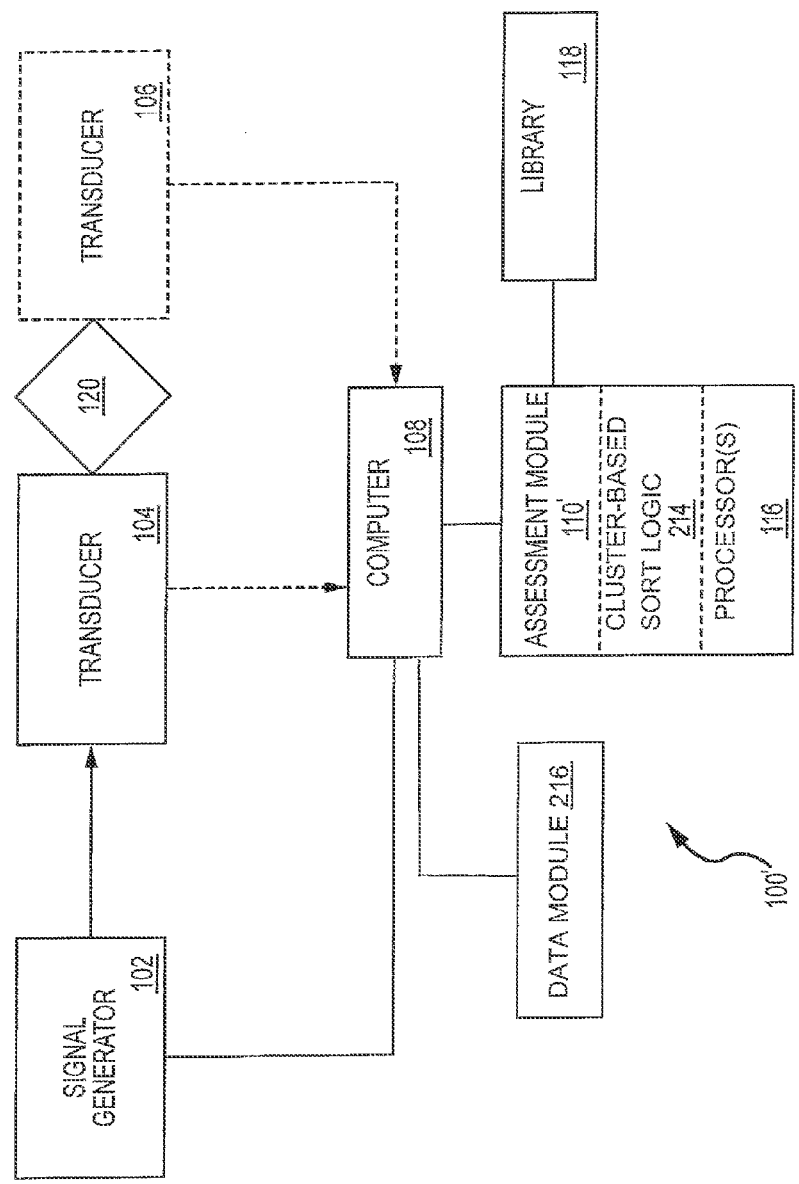
FIG. 6 is a block diagram of another embodiment of a resonance inspection tool that is configured to provide a cluster-based assessment of a part.

Another embodiment of a resonance inspection tool is illustrated in FIG. 6, is identified by reference numeral 100', and is a variation of the resonance inspection tool 100 discussed above. Unless otherwise noted, the discussion of the resonance inspection tool 100 is equally applicable to the resonance inspection tool 100', including without limitation with regard to the acquisition of vibration data on a part 120. However, the resonance inspection tool 100' of FIG. 6 does include a modified assessment module 110' (e.g., incorporated/embodied by a non-transitory computer-readable storage medium). Such an assessment module 110' includes at least a cluster-based sort logic 214 (the assessment module 110' may also include one or more features discussed above in relation to the assessment module 110 as well). The resonance inspection tool 100' also includes a data module 216 (e.g., a non-transitory computer-readable storage medium). Data of any appropriate type may be loaded into or otherwise acquired by the resonance inspection tool 100' through the data module 216. Frequency response data, alone or in combination with data of any other appropriate type (via the data module 216), may be used by the cluster-based sort logic 214. The cluster-based sort protocols of FIGS. 7, 9-11, 14, and 15 each use data in the form of a frequency response to assess a part. Each of these same cluster-based sort protocols may undertake an assessment based solely upon frequency response data. Each of these same cluster-based sort protocols may undertake an assessment based upon frequency response data and at least one other type of data.

A number of cluster-based sort protocols for classifying a part will now be addressed, and each of which may be incorporated/embodied by a non-transitory computer-readable storage medium (e.g., each such cluster-based sort protocol may be of a non-transitory form, and may be used/incorporated by a resonance inspection tool). Specifically, these sort protocols are configured to assign a part-under-test to either a first classification 210 or to a second classification 212. Generally, a part that is assigned to the first classification 210 is characterized as accepted or acceptable (e.g., based upon its frequency response), while a part that is assigned to the second classification 212 is characterized as rejected or unacceptable (e.g., based upon its frequency response). A part or cluster that is associated with a second classification 212 may be associated with a known defect or combination of defects (e.g., type and/or location, and that is reflected in the frequency response). However, a part or cluster that is associated with a second classification 212 may simply be associated with certain resonance data (e.g., a particular resonance characteristic or a particular set of resonance characteristics, such as the resonance frequency of one or more modes not fitting within the reference population, the resonance frequency pattern not matching that of the reference population, the frequency response displaying significant resonance degeneracy or change in amplitude or peak shape (Q)).

Figure 7:
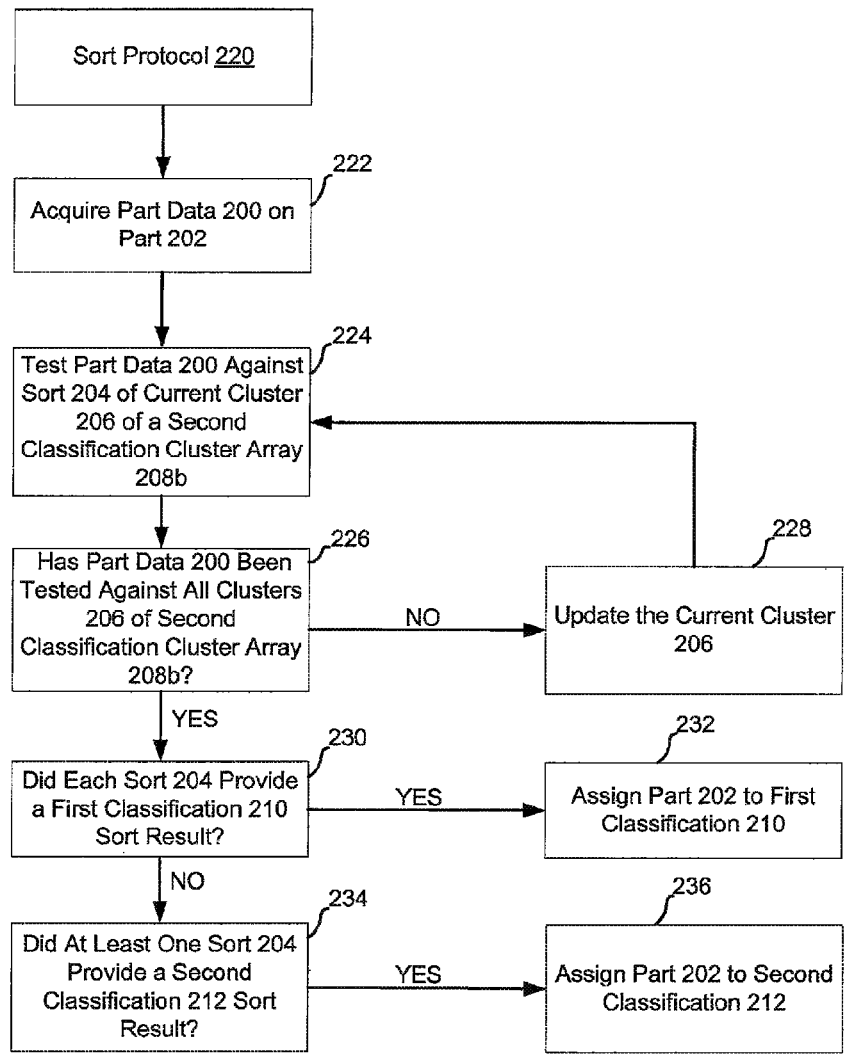
FIG. 7 is one embodiment of a cluster-based sort protocol that may be used by a resonance inspection tool.
Figure 8:
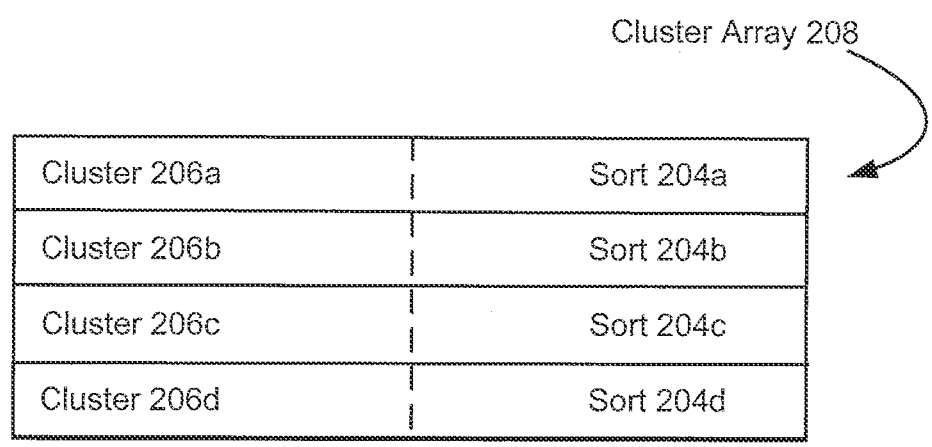
FIG. 8 is a schematic of one embodiment of a cluster array.

One embodiment of what may be characterized as a cluster-based sort protocol for classifying a part 202 (e.g., assigning the part 202 to a first classification 210; assigning the part 202 to a second classification 212) is presented in FIG. 7, is identified by reference numeral 220, and may be executed by any appropriate resonance inspection tool (e.g., resonance inspection tool 100 of FIG. 3; resonance inspection tool 100' of FIG. 6, where the cluster-based sort logic 214 may be configured in accordance with the sort protocol 220). Part data 200 (at least a frequency response or resonance data) is acquired for the part 202 pursuant to step 222 of the sort protocol 220. The part data 200 on the part 202 may be in accordance with the foregoing (e.g., where the part 202 is excited at a plurality of different input frequencies, and where the frequency response of the part 202 at each particular input frequency is incorporated by the frequency response for the part 202 and becomes at least part of the part data 200). The part data 200 (step 222) is tested against a plurality of sorts 204 of a second classification cluster array or group 208*b* in accordance with the sort protocol 220 of FIG. 7. FIG. 8 presents one embodiment of a generic cluster array 208. The cluster array 208 includes a plurality of clusters 206. Each cluster 206 has a dedicated sort 204. As the cluster array 208 includes a plurality of clusters 206, the cluster array 208 also thereby includes a plurality of sorts 204. Any appropriate number of clusters 206 may be incorporated by the cluster array 208, again where each cluster 206 includes a corresponding sort 204. In the cluster array 208 presented in FIG. 8, there are four clusters 206*a*-206*d* and four sorts 204*a*-204*d*, again where each cluster 206 includes its own corresponding sort 204 for the cluster array 208.

Each cluster 206 within a given cluster array 208 is defined by a plurality of clustered parts, where each of the clustered parts in a given cluster 206 have a common set of one or more attributes and/or one or more relationships (e.g., in relation to their respective frequency responses). All clusters 206 in a given cluster array 208 have clustered parts that are of the same overall classification (e.g., are of a common first classification 210 or are of a common second classification 212). Each cluster 206 in the cluster array 208 also may be characterized as exhibiting common clustering criteria (i.e., one or more clustering criterion). For instance, the parts of a given cluster 206 may exhibit a common resonance data pattern (parts may be clustered based upon at least a common resonance data pattern), where each of the clusters 206 is associated with a different corresponding resonance data pattern compared to all other clusters 206 in the cluster array 208. Parts in each given cluster 206 may also have a common resonance data pattern, and at least one other common clustering parameter such as a common manufacturer, common manufacturing data, common component data, and common service-related data.

In the case of the sort protocol 220 of FIG. 7, the cluster array that is used is a second classification cluster array 208*b*—a cluster array in accordance with FIG. 8 where each cluster 206 of the second classification cluster array 208*b* is of a second classification 212 (e.g., a rejected or unacceptable part classification). The part data 200 (step 222) is tested against the sort 204 for one of the clusters 206 of the second classification cluster array 208*b* pursuant to step 224. A sort 204 for a corresponding cluster 206 may be used to determine if the part data 200 matches the resonance data pattern of this cluster 206. A "sort 204", as used herein, thereby may be at least generally in accordance with the discussion of a resonance standard presented above. A sort 204 may be characterized as an algorithm or a combination of algorithms that are used to determine if at least one characteristic (e.g., an attribute and/or a relationship), and more typically to determine if a plurality of characteristics, exist in relation to the part data 200 (e.g., a frequency response). A sort 204 may be characterized as an algorithm or a combination of algorithms that are used to determine if frequency-based criteria (i.e., one or more frequency-based criterion) exist in relation to certain part data 200 that includes at least a frequency response of the part 202. For instance, a sort 204 may be configured to require a peak of at least a certain amplitude at one or more frequencies in a frequency response, the lack of any peak of at least a certain amplitude throughout one or more frequency ranges of a frequency response, a predetermined relationship between one or more peaks in a frequency response (e.g., an amplitude ratio threshold), and the like. A sort 204 may be configured to require a peak frequency within a given frequency range (where a "peak frequency" is a local amplitude maxima in the frequency response), may be configured to require that a given frequency range include a peak of at least a certain amplitude at one or more frequencies in a frequency response, may be configured to require the lack of any peak of at least a certain amplitude throughout one or more frequency ranges of a frequency response, may be configured to require a predetermined relationship between one or more peaks in a frequency response (e.g., an amplitude ratio threshold), may be configured to require a predetermined relationship between two or more peak frequencies (e.g., a certain ratio or delta between a pair of peak frequencies), or a combination thereof.

The sort protocol 220 of FIG. 7 (and other sort protocols addressed herein) is again directed to determining if a part 202 should be assigned to a first classification 210 (e.g., an accepted/acceptable part classification) or to a second classification 212 (e.g., a rejected, unacceptable part classification). With regard to this function and as used herein, the phrase "passing a sort 204" or the like may be associated with this particular sort 204 determining that the part 202 should be assigned to a first classification 210—the results of the sort 204 in this instance may indicate that the part 202 should be assigned to a first classification 210. Conversely, the phrase "failing a sort 204" or the like may be associated with this particular sort 204 determining that the part 202 should be assigned to a second classification 212—the results of the sort 204 in this instance may indicate that the part 202 should be assigned to a second classification 212.

In one embodiment, a sort 204 may be configured to determine if the part data 200 on a given part 202 exhibits frequency criteria that have been previously determined to be associated with the first classification 210. If the part data 200 on the part 202 exhibits the frequency criteria in this instance, the part 202 may be characterized as "passing the sort 204" (e.g., the result of this sort 204 is that the part 202 is associated with a first classification 210). In another embodiment, a sort 204 may be configured to determine if the part data 200 on a given part 202 excludes frequency criteria that have been previously determined to be associated with the second classification 212. If the part data 200 on the part 202 does not include the frequency criteria in this instance, the part 202 may be characterized as "passing the sort 204" (e.g., the result of this sort 204 is that the part 202 is associated with a first classification 210).

In another embodiment and if part data 200 is characterized as passing a sort 204, this may mean that the corresponding part 202 (more specifically its part data 200)

includes the characteristic or combination of characteristics embodied or required by the sort 204 (e.g., "passing a sort 204" may be associated with the part data 200 satisfying the criteria of the sort 204). Conversely and if part data 200 is characterized as failing a sort 204, this may mean that the corresponding part 202 (more specifically its part data 200) fails to include one or more characteristics that are embodied or required by the sort 204 (e.g., "failing a sort 204" may be associated with the part data 200 failing to satisfy the criteria of the sort 204).

Now referring back to the sort protocol 220 of FIG. 7, step 226 is directed toward determining if the part data 200 on the part 202 has been tested against all clusters 206 of the second classification cluster array 208b (more specifically tested against the corresponding sort 204 for each cluster 206 of the second classification cluster array 208b). If not, the cluster 206 is updated pursuant to step 228 (e.g., another cluster 206/corresponding sort 204 is selected), and control is returned to step 224 for repetition in accordance with the foregoing. On the first execution of step 224, the part data 200 on the part 202 may be tested against the sort 204a for the cluster 206a (FIG. 8) of the second classification cluster array 208b. If the part data 200 on the part 202 has not been tested against the sorts 204b-d (FIG. 8), the "updated cluster 206" for purposes of the first execution of step 228 of the sort protocol 220 may be the cluster 206b, and steps 224 and 226 may be repeated. It should be appreciated that the sort protocol 220 may sequence through the second classification cluster array 208b (e.g., FIG. 8) in any appropriate fashion so long as the part data 200 on the part 202 ends up being tested against each sort 204 of the second classification cluster array 208b (e.g., the sort protocol 220 may sequence through the second classification cluster array 208b in a top-to-down fashion and in one-step increments, or on any other appropriate basis).

Once step 226 of the sort protocol 220 of FIG. 7 determines that the part data 200 on the part 202 has been tested against all clusters 206 of the second classification cluster array 208b (i.e., has been tested against the sort 204 for all clusters 206 of the second classification cluster array 208b), control is transferred from step 226 to step 230. Step 230 is directed to determining if the sort results of each sort 204 of the second classification cluster array 208b are equated with a first classification 210. If each sort 204 of the second classification cluster array 208b provided a first classification 210 sort result, the sort protocol 220 proceeds from step 230 to step 232 where the part 202 is assigned to the first classification 210. If step 230 of the sort protocol 220 determines that each sort 204 of the second classification cluster array 208b did not provide a first classification 210 sort result, the sort protocol 220 proceeds from step 230 to step 234. Step 234 of the sort protocol 220 is directed to determining if at least one sort 204 of the second classification cluster array 208b provided a sort result that is equated with a second classification 212. If step 234 of the sort protocol 220 determines that at least one sort 204 of the second classification cluster array 208b provided a second classification 212 sort result, the sort protocol 220 proceeds from step 234 to step 236 where the part 202 is assigned to the second classification 212.

Steps 230 and 234 of the sort protocol 220 may be executed in any order. In addition, the sort protocol 220 may be configured to include only one of steps 230 and 234. For instance, if only step 230 is used and determines that each sort 204 of the second classification cluster array 208b did not provide a first classification 210 sort result, the sort protocol 220 may be configured to assign a second classification 212 to the part 202. If only step 234 is used and determines that none of the sorts 204 of the second classification cluster array 208b provided a second classification 212 sort result, the sort protocol 220 may be configured to assign a first classification 210 to the part 202. In any case, a given part 202 will be assigned to either the first classification 210 or to the second classification 212 pursuant to the sort protocol 220 of FIG. 7.

Figure 9:
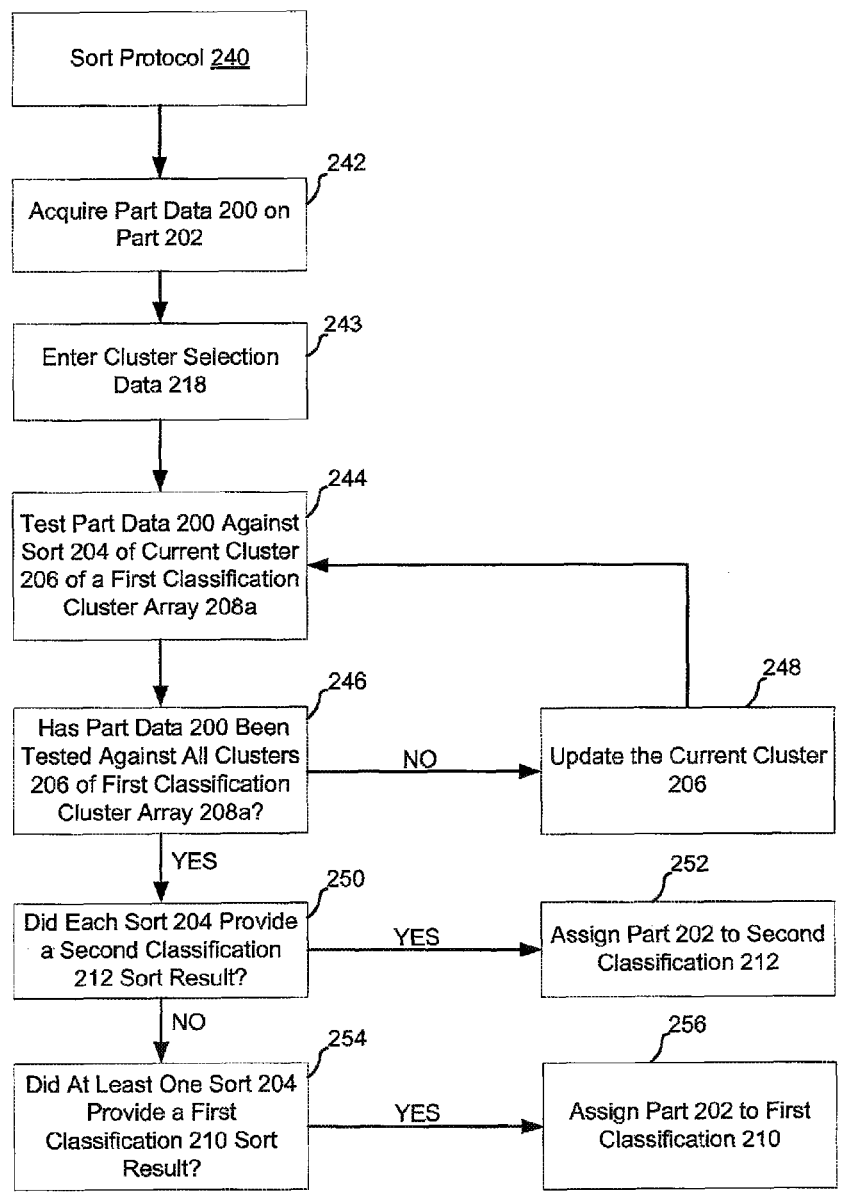
FIG. 9 is another embodiment of a cluster-based sort protocol that may be used by a resonance inspection tool.

Another embodiment of what may be characterized as a cluster-based sort protocol for classifying a part 202 (e.g., assigning the part 202 to a first classification 210; assigning the part 202 to a second classification 212) is presented in FIG. 9, is identified by reference numeral 240, and may be executed by any appropriate resonance inspection tool (e.g., resonance inspection tool 100 of FIG. 3; resonance inspection tool 100' of FIG. 6, where the cluster-based sort logic 214 may be configured in accordance with the sort protocol 240). Part data 200 (at least a frequency response or resonance data) is acquired on the part 202 pursuant to step 242 of the sort protocol 240. The part data 200 on the part 202 may be in accordance with the foregoing (e.g., where the part 202 is excited at a plurality of different input frequencies, and where the response of the part 202 at each particular input frequency is incorporated by the frequency response for the part 202 and becomes at least part of the part data 200).

Cluster selection data 218 may be input (e.g., to the resonance inspection tool 100') by a user in accordance with optional step 243 of the sort protocol 240 (i.e., step 243 is not required in all instances). This "cluster selection data 218" may be any appropriate data that may be used to define a first classification cluster array 208a—a cluster array in accordance with FIG. 8 where each cluster 206 of the first classification cluster array 208a is of a first classification 210 (e.g., an accepted or acceptable part classification). Exemplary cluster selection data 218 includes manufacturer data, manufacturing data, specified component data, and specified service-related data, individually and in each combination, and each of which is addressed in more detail below. As such, the first classification cluster array 208a for purposes of the sort protocol 240 of FIG. 9 (where step 243 is used) could include one or more clusters 206 that each have a different corresponding resonance data pattern compared to every other cluster 206 in the first classification cluster array 208a, and in addition each given cluster 206 could include a plurality of parts that are each of the first classification 210, that each have a common resonance data pattern, and furthermore that each comply with all cluster selection data 218 that may be provided pursuant to step 243. In the case where cluster selection data 218 is used by the sort protocol 240, corresponding data on the part 202 may be acquired pursuant to step 242. However, step 243 again is optional (regarding cluster selection data 218), so the assessment of the part 202 by the sort protocol 240 could be based solely on its frequency response or resonance data.

In the case of the sort protocol 240 of FIG. 9, the cluster array that is used is a first classification cluster array 208a—a cluster array in accordance with FIG. 8 where each cluster 206 of the first classification cluster array 208a is of a first classification 210 (e.g., an accepted or acceptable part classification). The part data 200 (step 242) is tested against the sort 204 for one of the clusters 206 of the first classification cluster array 208a pursuant to step 244. Step 246 of the sort protocol 240 of FIG. 9 is directed toward determining if the part data 200 on the part 202 has been tested against all clusters 206 of the first classification cluster array 208a (more specifically tested against the corresponding sort 204 for each cluster 206 of the first classification cluster array 208a). If not, the cluster 206 is updated pursuant to step 248 (e.g., another cluster 206/corresponding sort 204 is selected), and control is returned to step 244 for repetition in accordance with the foregoing. On the first execution of step 244, the part data 200 on the part 202 may be tested against the sort 204a for the cluster 206a (FIG. 8) of the first classification cluster array 208a. If the part data 200 on the part 202 has not been tested against the sorts 204b-d (FIG. 8), the "updated cluster 206" for purposes of the first execution of step 248 may be the cluster 206b, and steps 244 and 246 may be repeated. It should be appreciated that the sort protocol 240 may sequence through the first classification cluster array 208a in any appropriate fashion so long as the part data 200 on the part 202 ends up being tested against each sort 204 of the first classification cluster array 208a (e.g., the sort protocol 240 may sequence through the first classification cluster array 208a in a top-to-down fashion and in one-step increments, or on any other appropriate basis).

Once step 246 of the sort protocol 220 of FIG. 9 determines that the part data 200 on the part 202 has been tested against all clusters 206 of the first classification cluster array 208a (i.e., has been tested against the sort 204 for all clusters 206 of the first classification cluster array 208a), control is transferred from step 246 to step 250. Step 250 is directed to determining if the sort results of each sort 204 of the first classification cluster array 208a was equated with a second classification 212. If each sort 204 of the first classification cluster array 208a provided a second classification 212 sort result, the sort protocol 240 proceeds from step 250 to step 252 where the part 202 is assigned a second classification 212. If step 250 of the sort protocol 240 determines that each sort 204 of the first classification cluster array 208a did not provide a second classification 212 sort result, the sort protocol 240 proceeds from step 250 to step 254. Step 254 of the sort protocol 240 is directed to determining if at least one sort 204 of the first classification cluster array 208a provided a sort result that is equated with a first classification 210. If step 254 of the sort protocol 240 determines that at least one sort 204 of the first classification cluster array 208a provided a first classification 210 sort result, the sort protocol 240 proceeds from step 254 to step 256 where the part 202 is assigned a first classification 210.

Steps 250 and 254 of the sort protocol 240 may be executed in any order. In addition, the sort protocol 240 may be configured to include only one of steps 250 and 254. For instance, if only step 250 is used and determines that each sort 204 of the first classification cluster array 208a did not provide a second classification 212 sort result, the sort protocol 240 may be configured to assign a first classification 210 to the part 202. If only step 254 is used and determines that none of the sorts 204 of the first classification cluster array 208a provided a first classification 210 sort result, the sort protocol 240 may be configured to assign a second classification 212 to the part 202. In any case, a given part 202 will be assigned to either the first classification 210 or to the second classification 212 pursuant to the sort protocol 240 of FIG. 9.

Figure 10:
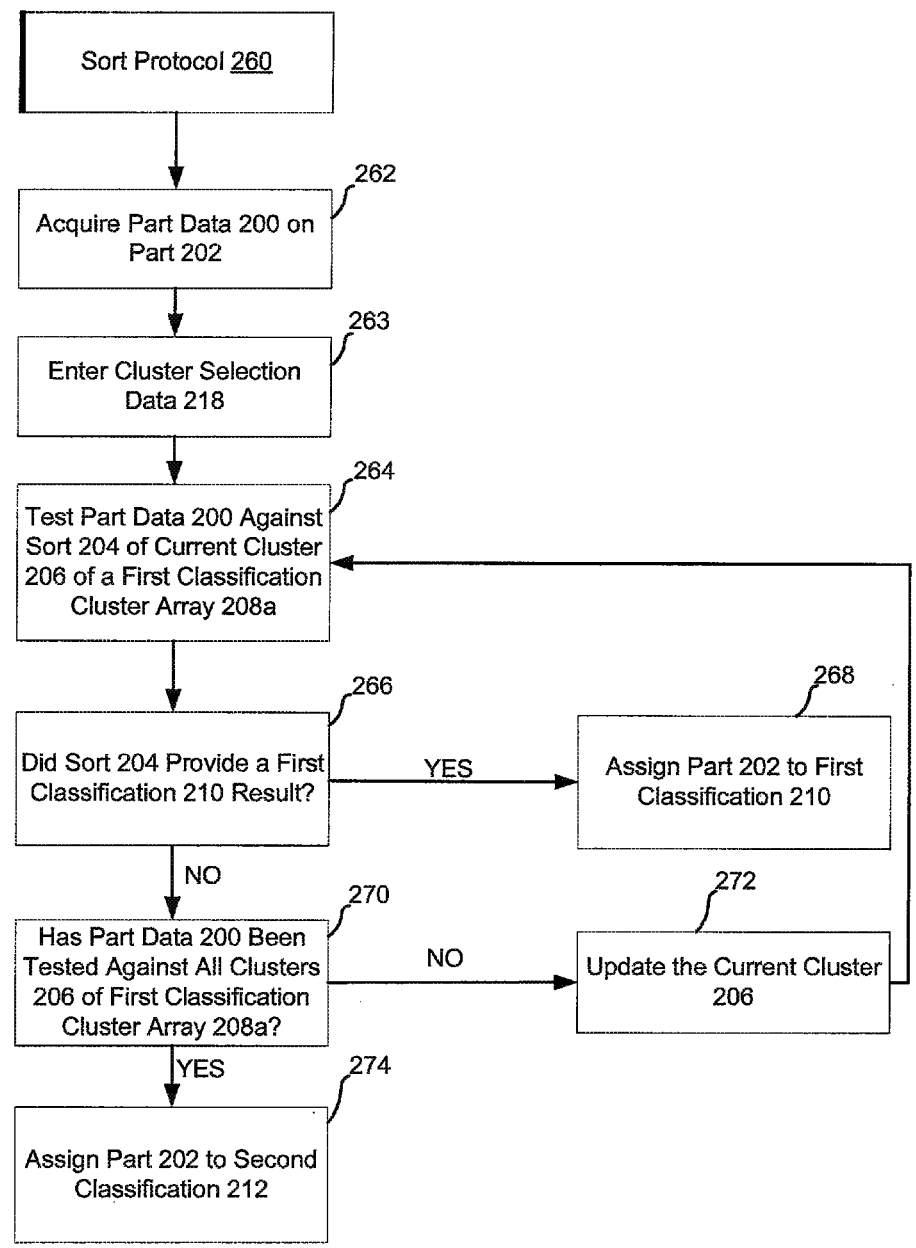
FIG. 10 is another embodiment of a cluster-based sort protocol that may be used by a resonance inspection tool.

Another embodiment of what may be characterized as a cluster-based sort protocol for classifying a part 202 (e.g., assigning the part 202 to a first classification 210; assigning the part 202 to a second classification 212) is presented in FIG. 10, is identified by reference numeral 260, and may be executed by any appropriate resonance inspection tool (e.g., resonance inspection tool 100 of FIG. 3; resonance inspection tool 100' of FIG. 6, where the cluster-based sort logic 214 may be configured in accordance with the sort protocol 260). Part data 200 (at least a frequency response or resonance data) is acquired on the part 202 pursuant to step 262 of the protocol 260. The part data 200 on the part 202 may be in accordance with the foregoing (e.g., where the part 202 is excited at a plurality of different input frequencies, and where the response of the part 202 at each particular input frequency is incorporated by the frequency response for the part 202 and becomes at least part of the part data 200).

Cluster selection data 218 may be input (e.g., to the resonance inspection tool 100') by a user in accordance with optional step 263 of the sort protocol 260 (i.e., step 263 is not required in all instances). This "cluster selection data 218" may be any appropriate data that may be used to define a first classification cluster array 208a—a cluster array in accordance with FIG. 8 where each cluster 206 of the first classification cluster array 208a is of a first classification 210 (e.g., an accepted or acceptable part classification). Exemplary cluster selection data 218 includes manufacturer data, manufacturing data, specified component data, and specified service-related data, individually and in each combination, and each of which is addressed in more detail below. As such, the first classification cluster array 208a for purposes of the sort protocol 260 of FIG. 10 (where step 263 is used) could include one or more clusters 206 that each have a different corresponding resonance data pattern compared to every other cluster 206 in the first classification cluster array 208a, and in addition each given cluster 206 could include a plurality of parts that are each of the first classification 210, that each have a common resonance data pattern, and furthermore that each comply with all cluster selection data 218 that may be provided pursuant to step 263. In the case where cluster selection data 218 is used by the sort protocol 260, corresponding data on the part 202 may be acquired pursuant to step 262. However, step 263 again is optional (regarding cluster selection data 218), so the assessment of the part 202 by the sort protocol 260 could be based solely on its frequency response or resonance data.

In the case of the sort protocol 260 of FIG. 10, the cluster array that is used again is a first classification cluster array 208a—each cluster 206 of the first classification cluster array 208a is of a first classification 210 (e.g., an accepted or acceptable part classification). The part data 200 (step 262) is tested against the sort 204 for one of the clusters 206 of the first classification cluster array 208a pursuant to step 264. Step 266 of the sort protocol 260 is directed to determining if the current sort 204 of the first classification cluster array 208a (step 264) provided a sort result that is equated with a first classification 210. If step 266 of the sort protocol 260 determines that the sort 204 (step 264) of the first classification cluster array 208a provided a first classification 210 sort result, the sort protocol 260 proceeds from step 266 to step 268 where the part 202 is assigned a first classification 210. Otherwise, control of the sort protocol 260 of FIG. 10 instead proceeds from step 266 to step 270 (versus step 268 discussed above). Step 270 of the sort protocol 260 is directed toward determining if the part data 200 on the part 202 has been tested against all clusters 206 of the first classification cluster array 208a (more specifically tested against the corresponding sort 204 for each cluster 206 of the first classification cluster array 208a). If not, the cluster 206 is updated pursuant to step 272 (e.g., another cluster/corresponding sort 204 is selected), and control is returned to step 264 for repetition in accordance with the foregoing. On the first execution of step 264, the part data 200 on the part 202 may be tested against the sort 204a for the cluster 206a (FIG. 8) of the first classification cluster array 208a. If the part data 200 on the part 202 did not pass the sort 204a and if the part 202 has not yet been tested against the sorts 204b-d (FIG. 8), the "updated cluster 206" for purposes of the first execution of step 272 may be the cluster 206b, and steps 264 and 266 may then be repeated. It should be appreciated that the sort protocol 260 may sequence through the first classification cluster array 208a in any appropriate fashion (e.g., the sort protocol 260 may sequence through the first classification cluster array 208a in a top-to-down fashion and in one-step increments, or on any other appropriate basis).

If the sort protocol 260 does not reach step 268 for any sort 204 of the first classification cluster array 208a, control is transferred from steps 266/270 of the sort protocol 260 to step 274. Pursuant to step 274, the part 202 is assigned to a second classification 212. In accordance with the sort protocol 260, a given part 202 will thereby be assigned to either the first classification 210 or to the second classification 212 pursuant to the sort protocol 240 of FIG. 10.

Figure 11:
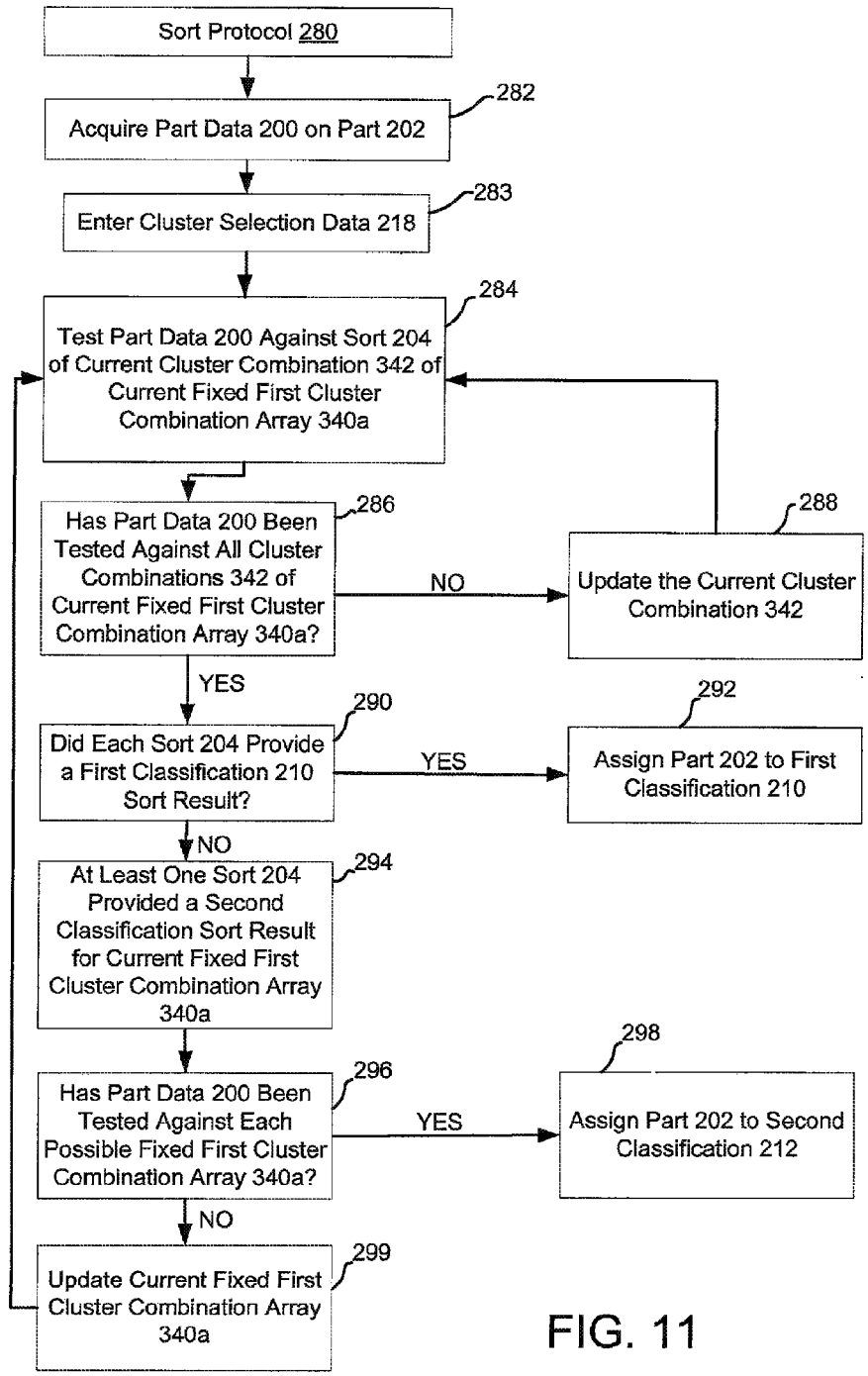
FIG. 11 is one embodiment of a cluster combination-based sort protocol that may be used by a resonance inspection tool, and that utilizes one or more fixed first cluster combination arrays of the type shown in FIG. 13A.

One embodiment of what may be characterized as cluster combination-based sort protocol for classifying a given part 202 (e.g., assigning the part 202 to a first classification 210; assigning the part 202 to a second classification 212) is presented in FIG. 11, is identified by reference numeral 280, and may be executed by any appropriate resonance inspection tool (e.g., resonance inspection tool 100 of FIG. 3; resonance inspection tool 100' of FIG. 6, where the cluster-based sort logic 214 may be configured in accordance with the sort protocol 280). Part data 200 (at least a frequency response or resonance data) is acquired for the part 202 pursuant to step 282 of the protocol 280. The part data 200 on the part 202 may be in accordance with the foregoing (e.g., where the part 202 is excited at a plurality of different input frequencies, and where the response of the part 202 at each particular input frequency is incorporated by the frequency response for the part 202 and becomes at least part of the part data 200).

Figure 12:
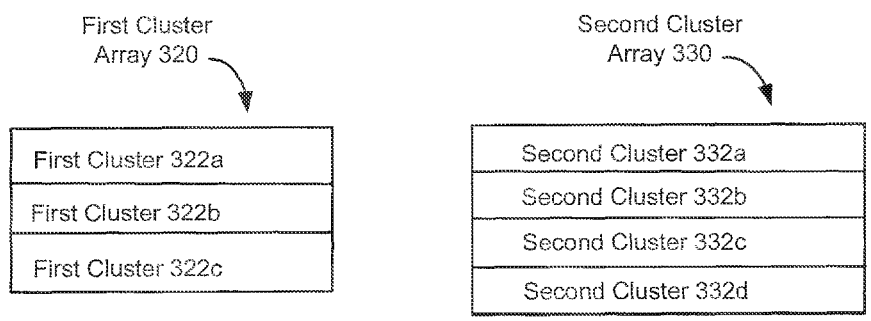
FIG. 12 is a schematic of a first cluster array and a second cluster array.

The part data 200 (step 282) is tested against a plurality of sorts 204 of a fixed first cluster combination array or group 340a in accordance with the sort protocol 280 of FIG. 11. Such a fixed first cluster combination array 340a may be described in relation to FIGS. 12 and 13A. FIG. 12 presents a first cluster array 320 having a plurality of first clusters (322a, 322b, and 322c in the illustrated embodiment), along with a second cluster array 330 having a plurality of second clusters (332a, 332b, 332c, and 332d in the illustrated embodiment). Any appropriate number of first clusters may be incorporated by the first cluster array 320 (three in the illustrated embodiment), and any appropriate number of second clusters may be incorporated by the second cluster array 330 (four in the illustrated embodiment). Each first cluster of the first cluster array 320 includes a plurality of first clustered parts (each of which is of a first classification 210, and where the first clustered parts in each given first cluster exhibit a common resonance data pattern), and each second cluster of the second cluster array 320 includes a plurality of second clustered parts (each of which is of a second classification 212, and where the second clustered parts in each given second cluster exhibit a common resonance data pattern).

Any appropriate number of first clustered parts may be used by each first cluster of the first cluster array 320, and any appropriate number of second clustered parts may be used by each second cluster of the second cluster array 330. Each first cluster of the first cluster array 320 may have a different corresponding resonance data pattern relative to every other first cluster in the first cluster array 320 and also relative to each second cluster in the second cluster array 330. Similarly, each second cluster of the second cluster array 330 may have a different corresponding resonance data pattern relative to every other second cluster in the second cluster array 330 and also relative to each first cluster in the first cluster array 320. Parts of each given first cluster of the first cluster array 320, as well as parts of each given second cluster of the second cluster array 330, may be clustered based solely on a common resonance data pattern, or these parts may be clustered based on a common resonance data pattern and at least one other common clustering parameter such as a common manufacturer, common manufacturing data, common component data, and common service-related data.

Figures 13A, 13B:
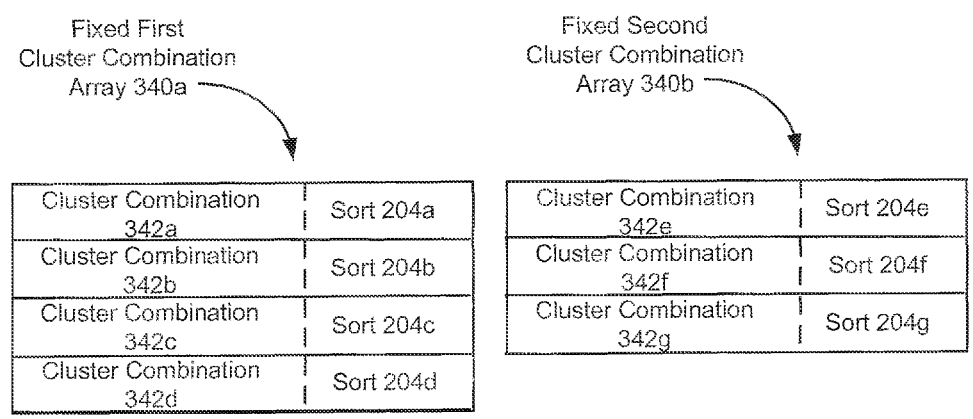
FIG. 13A is a schematic of a fixed first cluster combination array that may be defined from one of the first clusters of the first cluster array of FIG. 12 and the entirety of the second cluster array of FIG. 12.
FIG. 13B is a schematic of a fixed second cluster combination array that may be defined from one of the second clusters of the second cluster array of FIG. 12 and the entirety of the first cluster array of FIG. 12.

FIG. 13A presents a fixed first cluster combination array 340a that may be defined from the first cluster array 320 and the second cluster array 330 of FIG. 12. Generally, each fixed first cluster combination array 340a is defined by one of the first clusters from the first cluster array 320 (which again may include any appropriate number of first clusters), in combination with each second cluster from the second cluster array 330 (which again may include any appropriate number of second clusters). As such, three different fixed first cluster combination arrays 340a are possible from the first cluster array 320 and the second cluster array 330 of FIG. 12.

Each cluster combination 342 for the fixed first cluster combination array 340a (FIG. 13A) is provided by a different combination of the same first cluster from the first cluster array 320 and one second cluster from the second cluster array 330 (FIG. 12). Each cluster combination 342 of the fixed first cluster combination array 340a also has a different/dedicated sort 204 (FIG. 13A) compared to all other cluster combinations 342 of the fixed first cluster combination array 340a. As the fixed first cluster combination array 340a includes a plurality of cluster combinations 342 (4 in the illustrated embodiment of FIG. 13A), the fixed first cluster combination array 340a also thereby includes a plurality of different sorts 204 (4 in the illustrated embodiment of FIG. 13A). Generally, the fixed first cluster combination array 340a will have a number of cluster combinations 342 (and a corresponding sort 204) that is equal to the number of clusters within the second cluster array 330.

The fixed first cluster combination array 340a of FIG. 13A presents all possible combinations of the same first cluster from the first cluster array 320 (first classification 210) and each second cluster from the second cluster array 330 (second classification 212). Such a fixed first cluster combination array 340a may be defined in this manner using any of the first clusters 322 from the first cluster array 320. Cluster combination 342a of the fixed first cluster combination array 340a may be defined by the first cluster 322a and the second cluster 332a, and has a corresponding sort 204a. Cluster combination 342b of the fixed first cluster combination array 340a may be defined by the first cluster 322a and the second cluster 332b, and has a corresponding sort 204b. Cluster combination 342c of the fixed first cluster combination array 340a may be defined by the first cluster 322a and the second cluster 332c, and has a corresponding sort 204c. Cluster combination 342d of the fixed first cluster combination array 340a may be defined by the first cluster 322a and the second cluster 332d, and has a corresponding sort 204d. The other possible fixed first cluster combination arrays 340a may be defined in this same manner (a total of three different fixed first cluster combination arrays 340a may be defined from the illustrated first cluster array 320 and second cluster array 330 shown in FIG. 12).

The first cluster array 320 that is used to generate each fixed first cluster combination array 340*a* may be defined from cluster selection data 218 in accordance with the sort protocol 280 of FIG. 11. In this regard, cluster selection data 218 may be input (e.g., to the resonance inspection tool 100') by a user in accordance with optional step 283 of the sort protocol 280 (i.e., step 283 is not required in all instances). This "cluster selection data 218" may be any appropriate data that may be used to further define the first cluster array 320—a cluster array in accordance with FIG. 12 where each first cluster of the first cluster array 320 is of a first classification 210 (e.g., an accepted or acceptable part classification). Exemplary cluster selection data 218 includes manufacturer data, manufacturing data, specified component data, and specified service-related data, individually and in each combination, and each of which is addressed in more detail below. As such, the first cluster array 320 for purposes of the sort protocol 280 of FIG. 11 (where step 283 is used) may include one or more first clusters that each have a different corresponding resonance data pattern, and in addition each given first cluster could include a plurality of parts that are each of the first classification 210, that each have a common resonance data pattern, and furthermore that each comply with all cluster selection data 218 that may be provided pursuant to step 283. In the case where cluster selection data 218 is used by the sort protocol 280, corresponding data on the part 202 may be acquired pursuant to step 282. However, step 283 again is optional (regarding cluster selection data 218), so the assessment of the part 202 by the sort protocol 280 could be based solely on its frequency response or resonance data.

The part data 200 (step 282) is tested against the sort 204 for one of the cluster combinations 342 of the current fixed first cluster combination array 340*a* pursuant to each execution of step 284 for the sort protocol 280 of FIG. 11. The various sorts 204 for purposes of the fixed first cluster combination array 340*a* may be viewed as simultaneously assessing two different clusters (e.g., the same first cluster from the first cluster array 320 (first classification 210) and one second cluster from the second cluster array 330 (second classification 212), shown in FIG. 12). A plurality of parts may be separated into a plurality of different clusters on a common first basis for purposes of the first cluster array 320, but where all clustered parts in the first cluster array 320 are of a first classification 210 (including where each cluster is associated with a different manufacturer as will be discussed below in relation to the sort protocol 350 of FIG. 15). A plurality of parts may be separated into a plurality of different clusters on a common second basis for purposes of the second cluster array 330, but where all clustered parts in the second cluster array 330 are of a second classification 212.

As each sort 204 from the fixed first cluster combination array 340*a* at least in effect simultaneously assesses two different clusters (e.g., the same first cluster from the first cluster array 320 and one second cluster from the second cluster array 330 of FIG. 12), a sort 204 for purposes of the fixed first cluster combination array 340*a* of FIG. 12A (and for use by the sort protocol 280 of FIG. 11) may be characterized as being configured to: 1) provide a discrimination function in relation to clustered parts in one of the first clusters of the first cluster array 320; and 2) also provide a discrimination function in relation to clustered parts in one of the second clusters of the second cluster array 330. Generally, the sort protocol 280 of FIG. 11 is directed to determining if the part 202 should be assigned to the first classification 210 (e.g., an accepted/acceptable part classification) or to the second classification 212 (e.g., a rejected/unacceptable part classification). With regard to this function and as used herein, the phrase "passing a sort 204" or the like may be associated with this particular sort 204 determining that the part 202 should be assigned to a first classification 210—the results of the sort 204 in this instance may indicate that the part 202 should be assigned to a first classification 210. Conversely, the phrase "failing a sort 204" or the like may be associated with this particular sort 204 determining that the part 202 should be assigned to a second classification 212—the results of the sort 204 in this instance may indicate that the part 202 should be assigned to a second classification 212.

A given sort 204 for purposes of the sort protocol 280 and the fixed first cluster combination array 340*a* may be characterized as "passing" in relation to the testing of a certain part 202 against the sort 204: 1) if the predetermined attributes and/or relationships of the clustered parts in the particular first cluster of the first cluster array 320 exist in the part data 200 on the part 202; and 2) if the part data 200 on the part 202 excludes the predetermined attributes and/or relationships of the clustered parts in the particular second cluster of the second cluster array 330. Otherwise, the testing of this part 202 (e.g., its part data 200) against the sort 204 may be deemed to have failed the sort 204.

Step 286 of the sort protocol 280 of FIG. 11 is directed toward determining if the part data 200 on the part 202 has been tested against all cluster combinations 342 of the current fixed first cluster combination array 340*a*. If not, the cluster combination 342 is updated pursuant to step 288 (e.g., another cluster combination 342/sort 204 is selected), and control is returned to step 284 for repetition in accordance with the foregoing. On the first execution of step 284, the part data 200 on the part 202 may be tested against the sort 204*a* for the cluster combination 342*a* of the current fixed first cluster combination array 340*a* (FIG. 13A). As the part data 200 on the part 202 would not have been tested against the sorts 204*b-d* (FIG. 13A) in this example, the "updated cluster combination 342" for purposes of the first execution of step 288 may be the cluster combination 342*b* (FIG. 13A), and steps 284 and 286 may be repeated in accordance with the foregoing. This may be repeated in this manner for the entire current fixed first cluster combination array 340*a* (e.g., the sort protocol 280 may sequence through the current fixed first cluster combination array 340*a* in the top-to-down order presented in FIG. 13A and in one-step increments). It should be appreciated that the sort protocol 280 may sequence through the fixed first cluster combination array 340*a* in any appropriate fashion so long as the part data 200 on the part 202 is eventually tested against each sort 204 of the fixed first cluster combination array 340*a* (i.e., the sort protocol 280 does not have to test the part data 200 on the part 202 against the sorts 204 in the top-to-down order presented in FIG. 13A, and in one step increments).

Once step 286 of the sort protocol 280 of FIG. 11 determines that the part data 200 on the part 202 has been tested against all sorts 204 of the current fixed first cluster combination array 340*a*, control is transferred from step 286 to step 290. Step 290 is directed to determining if the sort results of each sort 204 of the current fixed first cluster combination array 340*a* is equated with a first classification 210. If each sort 204 of the fixed first cluster combination array 340*a* provided a first classification 210 sort result, the sort protocol 280 proceeds from step 290 to step 292 where the part 202 is assigned a first classification 210. If step 290 of the sort protocol 280 determines that each sort 204 of the current fixed first cluster combination array 340*a* did not provide a first classification 210 sort result, the sort protocol 280 proceeds from step 290 to steps 294 and step 296. Step 294 of the sort protocol 280 is merely indicating that at least one sort 204 of the current fixed first cluster combination array 340a provided a sort result that is equated with a second classification 212 pursuant to the decision that was made in step 290. As such, the sort protocol 280 does not actually take any action in relation to step 294.

Step 296 of the sort protocol 280 is directed to determining if the part data 200 has been tested against each possible fixed first cluster combination array 340a. When cluster selection data 218 is provided pursuant to step 283, the first cluster array 320 could have a single first cluster from which a single fixed first cluster combination array 340a may be generated, or the first cluster array 320 could have multiple first clusters from which a corresponding number of fixed first cluster combination arrays 340a may be generated. In any case, if the sort protocol 280 has provided at least one second classification 212 sort result within each possible fixed first cluster combination array 340a, the sort protocol 280 proceeds from step 296 to step 298 where the part 202 is assigned to the second classification 212. Otherwise, the sort protocol 280 proceeds from step 296 to step 299, which is directed to updating the current fixed first cluster combination array 340a (e.g., another fixed first cluster combination array 340a having corresponding sorts 204 is selected). The foregoing is then repeated for this new fixed first cluster combination array 340a (one execution of steps 284-298 may be for a fixed first cluster combination array 340a that is based upon the first cluster 322a; one execution of steps 284-298 may be for a fixed first cluster combination array 340a that is based upon the first cluster 322b; one execution of steps 284-298 may be for a fixed first cluster combination array 340a that is based upon the first cluster 322c).

Figure 14:
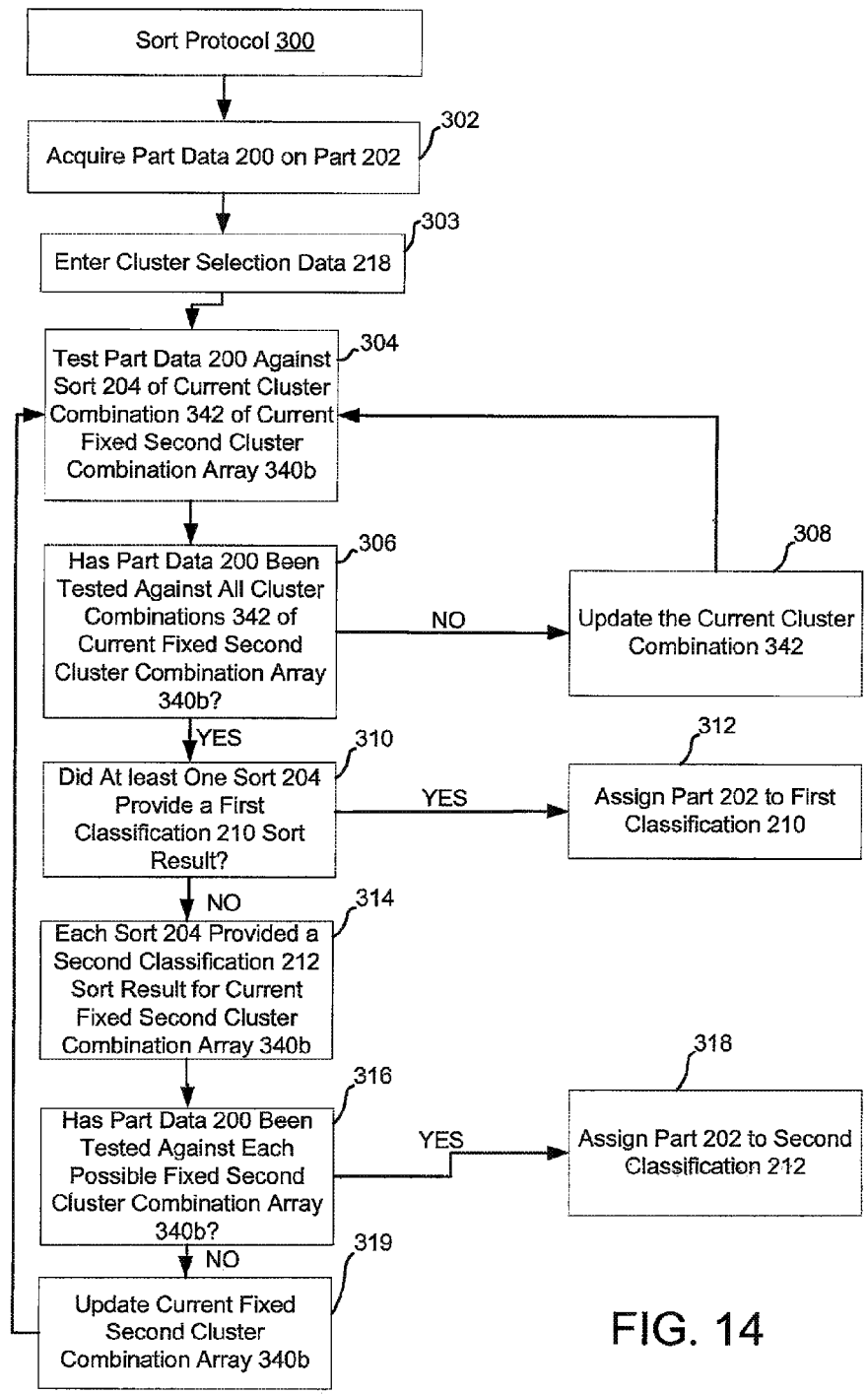
FIG. 14 is another embodiment of a cluster combination-based sort protocol that may be used by a resonance inspection tool, and that utilizes one or more fixed second cluster combination arrays of the type shown in FIG. 13B.

Another embodiment of what may be characterized as cluster combination-based sort protocol for classifying a given part 202 (e.g., assigning the part 202 to a first classification 210; assigning the part 202 to a second classification 212) is presented in FIG. 14, is identified by reference numeral 300, and may be executed by any appropriate resonance inspection tool (e.g., resonance inspection tool 100 of FIG. 3; resonance inspection tool 100' of FIG. 6, where the cluster-based sort logic 214 may be configured in accordance with the sort protocol 300). The sort protocol 300 uses a fixed second cluster combination array 340b that is also defined from the first cluster array 320 and the second cluster array 330 of FIG. 12. Generally, each fixed second cluster combination array 340b is defined by one of the second clusters from the second cluster array 330 (which again may include any appropriate number of second clusters), in combination with each first cluster from the first cluster array 320 (which again may include any appropriate number of first clusters). As such, three different fixed second cluster combination arrays 340b are possible from the first cluster array 320 and the second cluster array 330 of FIG. 12.

Each cluster combination 342 for the fixed second cluster combination arrays 340b (FIG. 13B) is provided by a different combination of the same second cluster from the second cluster array 330 and one first cluster from the first cluster array 320 (FIG. 12). Each cluster combination 342 of the fixed second cluster combination array 340b also has a different/dedicated sort 204 (FIG. 13B) compared to all other cluster combinations 342 of the fixed second cluster combination array 340b. As the fixed second cluster combination array 340b includes a plurality of cluster combinations 342 (3 in the illustrated embodiment of FIG. 13B), the fixed second cluster combination array 340b also thereby includes a plurality of different sorts 204 (3 in the illustrated embodiment of FIG. 13B). Generally, the fixed second cluster combination array 340b will have a number of cluster combinations 342 (and a corresponding sort 204) that is equal to the number of clusters within the first cluster array 320.

The fixed second cluster combination array 340b of FIG. 13B presents all possible combinations of the same second cluster from the second cluster array 330 (second classification 212) and each first cluster from the first cluster array 320 (first classification 210). Such a fixed second cluster combination array 340b may be defined in this manner using any of the second clusters 332 from the second cluster array 330. Cluster combination 342e of the fixed second cluster combination array 340b may be defined by the second cluster 332a and the first cluster 322a, and has a corresponding sort 204e. Cluster combination 342f of the fixed second cluster combination array 340b may be defined by the second cluster 332a and the first cluster 322b, and has a corresponding sort 204f. Cluster combination 342g of the fixed second cluster combination array 340b may be defined by the second cluster 332a and the first cluster 322c, and has a corresponding sort 204g. The other possible fixed second cluster combination arrays 340b may be defined in the same manner (a total of four different fixed second cluster combination arrays 340b may be defined from the illustrated first cluster array 320 and second cluster array 330 shown in FIG. 12).

Referring back to the sort protocol 300 of FIG. 14, part data 200 (at least a frequency response or resonance data) is acquired on the part 202 pursuant to step 302 of the protocol 300. The part data 200 on the part 202 may be in accordance with the foregoing (e.g., where the part 202 is excited at a plurality of different input frequencies, and where the response of the part 202 at each particular input frequency is incorporated by the frequency response for the part 202 and becomes at least part of the part data 200).

The first cluster array 320 that is used to generate each fixed second cluster combination array 340b may be defined from cluster selection data 218 in accordance with the sort protocol 300 of FIG. 14. In this regard, cluster selection data 218 may be input (e.g., to the resonance inspection tool 100') by a user in accordance with optional step 303 of the sort protocol 300 (i.e., step 303 is not required in all instances). This "cluster selection data 218" may be any appropriate data that may be used to further define the first cluster array 320—a cluster array in accordance with FIG. 12 where each first cluster of the first cluster array 320 is of a first classification 210 (e.g., an accepted or acceptable part classification). Exemplary cluster selection data 218 includes manufacturer data, manufacturing data, specified component data, and specified service-related data, individually and in each combination, and each of which is addressed in more detail below. As such, the first cluster array 320 for purposes of the sort protocol 300 of FIG. 14 (where step 303 is used) may include one or more first clusters that each have a different corresponding resonance data pattern, and in addition each given first cluster could include a plurality of parts that are each of the first classification 210, that each have a common resonance data pattern, and furthermore that each comply with all cluster selection data 218 that may be provided pursuant to step 303. In the case where cluster selection data 218 is used by the sort protocol 300, corresponding data on the part 202 may be acquired pursuant to step 302. However, step 303 again is optional (regarding cluster selection data 218), so the assessment of the part 202 by the sort protocol 300 could be based solely on its frequency response or resonance data.

The part data 200 (step 302) is tested against a plurality of sorts 204 of a current fixed second cluster combination array or group 340*b* (FIG. 13B) at generally in accordance with the sort protocol 280 of FIG. 11. As such, the discussion presented above regarding the sorts 204 for the sort protocol 280 of FIG. 11, including with regarding to passing/failing a particular sort 204, remains equally applicable to the sort protocol 300 of FIG. 14. In any case, the part data 200 on the part 202 (step 302) is tested against the sort 204 for one of the cluster combinations 342 from the current fixed second cluster combination array 340*b* pursuant to step 304.

The various sorts 204 for purposes of the fixed second cluster combination array 340*b* may be viewed as simultaneously assessing two different clusters (e.g., the same second cluster from the second cluster array 330 (second classification 212) and one first cluster from the first cluster array 320 (first classification 210), shown in FIG. 12). As noted, a plurality of parts may be separated into a plurality of different clusters on a common first basis for purposes of the first cluster array 320, but where all clustered parts in the first cluster array 320 are of a first classification 210 (including where each cluster is associated with a different manufacturer as will be discussed below in relation to the sort protocol 350 of FIG. 15). A plurality of parts may be separated into a plurality of different clusters on a common second basis for purposes of the second cluster array 330, but where all clustered parts in the second cluster array 330 are of a second classification 212.

As each sort 204 from the fixed second cluster combination array 340*b* at least in effect simultaneously assesses two different clusters (e.g., the same second cluster from the second cluster array 330 and one first cluster from the first cluster array 320 of FIG. 12), a sort 204 for purposes of the fixed second cluster combination array 340*b* of FIG. 13B (and for use by the sort protocol 300 of FIG. 14) may be characterized as being configured to: 1) provide a discrimination function in relation to clustered parts in one of the second clusters of the second cluster array 330; and 2) also provide a discrimination function in relation to clustered parts in one of the first clusters of the first cluster array 320. Generally, the sort protocol 300 of FIG. 14 is directed to determining if the part 202 should be assigned to the first classification 210 (e.g., an accepted/acceptable part classification) or to the second classification 212 (e.g., a rejected/unacceptable part classification). With regard to this function and as used herein, the phrase "passing a sort 204" or the like may be associated with this particular sort 204 determining that the part 202 should be assigned to a first classification 210—the results of the sort 204 in this instance may indicate that the part 202 should be assigned to a first classification 210. Conversely, the phrase "failing a sort 204" or the like may be associated with this particular sort 204 determining that the part 202 should be assigned to a different second classification 212—the results of the sort 204 in this instance may indicate that the part 202 should be assigned to a second classification 212.

A given sort 204 for purposes of the sort protocol 300 and the fixed second cluster combination array 340*b* may be characterized as "passing" in relation to the testing of a certain part 202 against the sort 204: 1) if the predetermined attributes and/or relationships of the clustered parts in the particular first cluster of the first cluster array 320 exist in the part data 200 on the part 202; and 2) if the part data on the part 202 excludes the predetermined attributes and/or relationships of the clustered parts in the particular second cluster of the second cluster array 330. Otherwise, the testing of this part 202 (e.g., its part data 200) against the sort 204 may be deemed to have failed the sort 204.

Step 306 of the sort protocol 300 of FIG. 14 is directed toward determining if the part data 200 on the part 202 has been tested against all cluster combinations 342 of the current fixed second cluster combination array 340*b*. If not, the cluster combination 342 is updated pursuant to step 308 (e.g., another cluster combination 342/sort 204 is selected), and control is returned to step 304 for repetition in accordance with the foregoing. On the first execution of step 304, the part data 200 on the part 202 may be tested against the sort 204*e* for the cluster combination 342*e* of the fixed second cluster combination array 340*b* (FIG. 13B). As the part data 200 on the part 202 would not have been tested against the sorts 204*f* and 204*g* (FIG. 13B) in this example, the "updated cluster combination 342" for purposes of the first execution of step 308 may be the cluster combination 342*f* (FIG. 13B), and steps 304 and 306 may be repeated in accordance with the foregoing. This may be repeated in this manner for the entire current fixed second cluster combination array 340*b* (e.g., the sort protocol 300 may sequence through the fixed second cluster combination array 340*b* in the top-to-down order presented in FIG. 13B and in one-step increments). However and in accordance with the foregoing, it should be appreciated that the sort protocol 300 may sequence through the current fixed second cluster combination array 340*b* in any appropriate fashion so long as the part data 200 on the part 202 is eventually tested against each sort 204 of the current fixed second cluster combination array 340*b* (i.e., the sort protocol 300 does not have to test the part data 200 on the part 202 against the sorts 204 in the top-to-down order presented in FIG. 13B and in one-step increments).

Once step 306 of the sort protocol 300 of FIG. 14 determines that the part data 200 on the part 202 has been tested against all sorts 204 of the current fixed second cluster combination array 340*b*, control is transferred from step 306 to step 310. Step 310 of the sort protocol 300 is directed to determining if at least one sort 204 of the current fixed second cluster combination array 340*b* provided a sort result that is equated with a first classification 210. If step 310 of the sort protocol 300 determines that at least one sort 204 of the current fixed second cluster combination array 340*b* provided a first classification 210 sort result, the sort protocol 300 proceeds from step 310 to step 312 where the part 202 is assigned a first classification 210. If step 310 of the sort protocol 300 determines that at least one sort 204 of the fixed second cluster combination array 340*b* did not provide a first classification 210 sort result, the sort protocol 300 proceeds from step 310 to steps 314 and 316. Step 314 of the sort protocol 300 is merely indicating that each sort 204 of the current fixed second cluster combination array 340*b* provided a sort result that is equated with a second classification 212 pursuant to the decision that was made in step 310. As such, the sort protocol 300 does not actually take any action in relation to step 314.

Step 316 of the sort protocol 300 is directed to determining if the part data 200 has been tested against each possible fixed second cluster combination array 340*b*. When cluster selection data 218 is provided pursuant to step 303, the first cluster array 320 could have a single first cluster in which case each fixed second cluster combination array 340*b* that may be generated would have a single cluster combination 342, or the first cluster array 320 could have multiple first clusters in which case each fixed second cluster combination array 340*b* that may be generated would have a corresponding number of cluster combinations 342. In any case, if the sort protocol 300 has provided a second classification 212 sort result throughout each possible fixed second cluster combination array 340*b*, the sort protocol 300 proceeds from step 316 to step 318 where the part 202 is assigned to the second classification 212. Otherwise, the sort protocol 300 proceeds from step 316 to step 319, which is directed to updating the current fixed second cluster combination array 340*b* (e.g., another fixed second cluster combination array 340*b* having corresponding sorts 204 is selected). The foregoing is then repeated for this new fixed second cluster combination array 340*b* (one execution of steps 304-318 may be for a fixed second cluster combination array 340*b* that is based upon the second cluster 332*a*; one execution of steps 304-318 may be for a fixed second cluster combination array 340*b* that is based upon the second cluster 332*b*; one execution of steps 304-318 may be for a fixed second cluster combination array 340*b* that is based upon the second cluster 332*c*; one execution of steps 304-318 may be for a fixed second cluster combination array 340*b* that is based upon the second cluster 332*d*).

Each of the second classification cluster array 208*b* (sort protocol 220 of FIG. 7), the first classification cluster array 208*a* (used by each of sort protocol 240 of FIG. 9 and the sort protocol 260 of FIG. 10), the first cluster array 320 (FIG. 12, and used by each of the sort protocol 280 of FIG. 11, the sort protocol 300 of FIG. 14, and the sort protocol 350 of FIG. 15), and the second cluster array 330 (FIG. 12, and used by each of the sort protocol 280 of FIG. 11, the sort protocol 300 of FIG. 14, and the sort protocol 350 of FIG. 15) may encompass a part population that is defined in any appropriate manner and on any appropriate basis, and where the part population may encompass a certain data range. The part population may be subdivided into a plurality of disjoint subsets or clusters within this data range (i.e., a given part can only be a member of one subset or cluster; each cluster may be specific to a certain portion of the data range), and the subsets/clusters may be complementary in relation to the data range of the part population (the various subsets/clusters may collectively encompass the entire data range of the part population).

One embodiment in accordance with the foregoing involves a part population for the case where the same part is available from multiple manufacturers, and where parts within this part population are then clustered for one or more of the noted cluster arrays 208*a*, 208*b*, 320, and 330 on a manufacturer-by-manufacturer basis (e.g., in addition to each part of the cluster array being of the first classification 210 or each part of the cluster array being of the second classification 212, the parts are further clustered on the basis of the manufacturer). Stated another way, a given cluster array may be defined entirely of parts that are from a set or collection of manufacturers of a common part, where each such part of the cluster array is of a common first classification 210 or a common second classification 212, and where each cluster of the cluster array is specific to a certain manufacturer of the part. As such, parts may be clustered on two separate clustering parameters—one clustering parameter being whether the part is of the first classification 210 or second classification 212 (all parts in a given cluster array being of a common classification), and the other clustering parameter being the manufacturer of the part. In this case, each part in a given cluster in this embodiment will have a common resonance data pattern, and each part will also be from a common manufacturer.

Another embodiment in accordance with the foregoing involves a part population that is based upon specified component data for the same part (e.g., one or more physical measurements of some type), where the specified component data of the individual parts varies throughout some acceptable data range for the part population (e.g., there is an acceptable variance in relation to a certain physical parameter(s) of the part), and where this data range is then subdivided into a plurality of disjoint subsets or clusters for one or more of the noted cluster arrays 208*a*, 208*b*, 320, and 330 (e.g., in addition to each part of the cluster array being of the first classification 210 or each part of the cluster array being of the second classification 212, the parts are further clustered on the basis of specified component data). Stated another way, a given cluster array may be defined entirely of parts that have specified component data within a certain data range, where each such part of the cluster array is of a common first classification 210 or a common second classification 212, and where each cluster of the cluster array is specific to a certain portion of this data range for the specified component data. As such, parts may be clustered on two separate clustering parameters—one clustering parameter being whether the part is of the first classification 210 or second classification 212 (all parts in a given cluster array being of a common classification), and the other clustering parameter being various non-overlapping ranges of specified component data. For example, the weight of the individual parts within a given cluster array may vary throughout an acceptable weight range, each cluster may be assigned to a disjoint subset/cluster within this weight range (i.e., a subset of the acceptable weight range for the part population), and the clusters may collectively define the entire weight range of the cluster array. There are of course other examples where component data can be used to define a given part population/cluster array, and where clusters within this cluster array may be defined based upon this component data. In any case, each part in a given cluster in this embodiment will have a common resonance data pattern, and each part will also have common specified component data.

Another embodiment in accordance with the foregoing involves a part population that is based upon specified manufacturing data for the same part (e.g., supplier/supplier location, equipment used, temperature settings, raw material lot number), where the specified manufacturing data of the individual parts varies throughout some acceptable data range for the part population (e.g., there is an acceptable variance in relation to the specified manufacturing data on the part), and where this data range is then subdivided into a plurality of disjoint subsets or clusters for one or more of the noted cluster arrays 208*a*, 208*b*, 320, and 330 (e.g., in addition to each part of the cluster array being of the first classification 210 or each part of the cluster array being of the second classification 212, the parts are further clustered on the basis of specified manufacturing data). Stated another way, a given cluster array may be defined entirely of parts that have specified manufacturing data within a certain data range, where each such part of the cluster array is of a common first classification 210 or a common second classification 212, and where each cluster of the cluster array is specific to a certain portion of this data range for the specified manufacturing data. As such, parts may be clustered on two separate clustering parameters—one clustering parameter being whether the part is of the first classification 210 or second classification 212 (all parts in a given cluster array being of a common classification), and the other clustering parameter being various non-overlapping ranges of specified manufacturing data. For instance, the part population may be defined by using a number of different machines to fabricate/manufacture the same part. Each cluster for a given cluster array 208a, 208b, 320, and 330 could be specific to a certain machine. The part population may be fabricated/manufactured from a variety of different raw material lot numbers. Each cluster for a given cluster array 208a, 208b, 320, and 330 could be specific to a certain raw material lot number. There are of course other examples where manufacturing data can be used to define a given part population/cluster array, and where clusters within this cluster array may be defined based upon this manufacturing data. In any case, each part in a given cluster in this embodiment will have a common resonance data pattern, and each part will also have common specified manufacturing data.

Another embodiment in accordance with the foregoing involves a part population that is based upon specified service-related data (e.g., how a given component was used, life cycle information, operating environment/conditions, repair status), where the specified service-related data of the individual parts varies throughout some acceptable data range for the part population (e.g., there is an acceptable variance in relation to the specified service-related data on the part), and where this data range is then subdivided into a plurality of disjoint subsets or clusters for one or more of the noted cluster arrays 208a, 208b, 320, and 330 (e.g., in addition to each part of the cluster array being of the first classification 210 or each part of the cluster array being of the second classification 212, the parts are further clustered on the basis of specified service-related data). Stated another way, a given cluster array may be defined entirely of parts that have specified service-related data within a certain data range, where each such part of the cluster array is of a common first classification 210 or a common second classification 212, and where each cluster of the cluster array is specific to a certain portion of this data range for the specified service-related data. As such, parts may be clustered on two separate clustering parameters—one clustering parameter being whether the part is of the first classification 210 or second classification 212 (all parts in a given cluster array being of a common classification), and the other clustering parameter being various non-overlapping ranges of specified service-related data. For instance, each cluster for a given cluster array 208a, 208b, 320, and 330 could be a different life cycle range. Each cluster for a given cluster array 208a, 208b, 320, and 330 could be dedicated to parts that are exposed to common operating and/or environmental conditions, and again where the operating and/or environmental conditions vary from cluster to cluster. There are of course other examples where different types of service-related data can be used to define a part population/cluster array, and where clusters may be defined based upon this service-related data. In any case, each part in a given cluster in this embodiment will have a common resonance data pattern, and each part will also have common specified service-related data.

In the case of any of the sort protocols addressed herein that use both a first cluster array 320 and a second cluster array 330, the first clusters 322 (first cluster array 320) and the second clusters 332 (second cluster array 330) may be clustered on the same basis (other than first classification 210/second classification 212), or the first clusters 322 (first cluster array 320) and the second clusters 332 (second cluster array 330) may be clustered on a different basis (in addition to first classification 210/second classification 212). Consider a first example where a given first cluster array 320 (parts of a first classification 210) is clustered based upon the manufacturer (i.e., each first cluster 322 is a different manufacturer). In this first example the corresponding second cluster array 330 (parts of a second classification 212) could be clustered based upon the manufacturer as well (i.e., each second cluster 332 could be specific to a different manufacturer and one or more defects), or the corresponding second cluster array 330 (parts of a second classification 212) could be clustered based strictly on a defect basis (e.g., each second cluster 332 could be specific to a certain defect or set of defects, and without regard to the manufacturer). Consider a second example where a given first cluster array 320 (parts of a first classification 210) is clustered based upon specified component data (i.e., each first cluster 322 is associated with different specified component data). In this second example the corresponding second cluster array 330 (parts of a second classification 212) could be clustered using specified component data (i.e., each second cluster 332 could be specific to different specified component data and one or more defects), or the corresponding second cluster array 330 could be clustered based strictly on a defect basis (e.g., each second cluster 332 could be specific to a certain defect or set of defects and without regard to specified component data). Consider a third example where a given first cluster array 320 (parts of a first classification 210) is clustered based upon specified manufacturing data (i.e., each first cluster 322 is associated with different specified manufacturing data). In this third example the corresponding second cluster array 330 (parts of a second classification 212) could be clustered using specified manufacturing data (i.e., each second cluster 332 could be specific to different specified manufacturing data and one or more defects), or the corresponding second cluster array 330 could be clustered based strictly on a defect basis (e.g., each second cluster 332 could be specific to a certain defect or set of defects and without regard to manufacturing data). Consider a fourth example where a given first cluster array 320 (parts of a first classification 210) is clustered based upon specified service-related data (i.e., each first cluster 322 is associated with different specified service-related data). In this fourth example the corresponding second cluster array 330 (parts of a second classification 212) could be clustered using specified service-related data (i.e., each second cluster 332 could be specific to different specified service-related data and one or more defects), or the corresponding second cluster array 330 could be clustered based strictly on a defect basis (e.g., each second cluster 332 could be specific to a certain defect or set of defects and without regard to specified component data).

Figure 15:
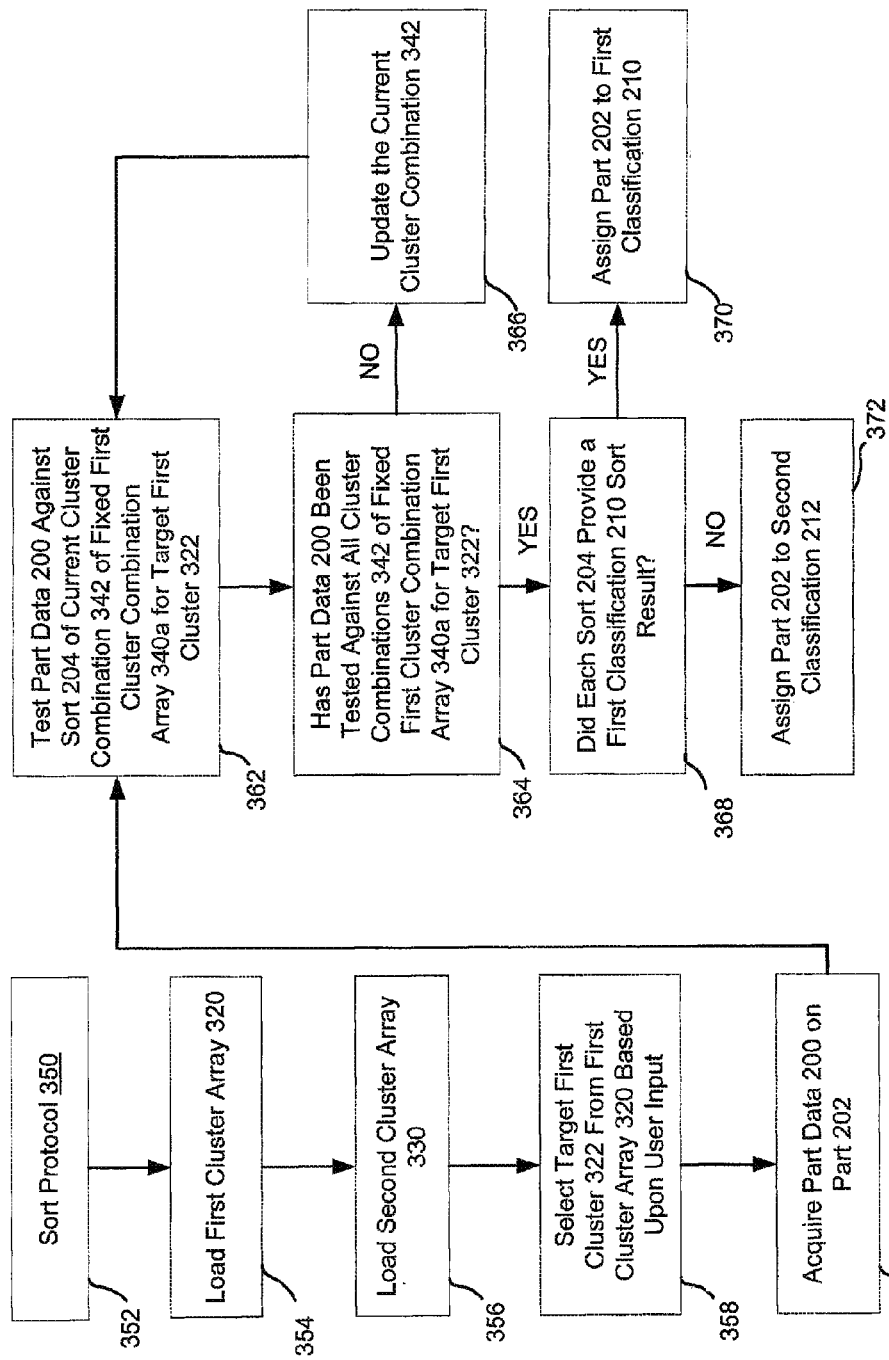
FIG. 15 is another embodiment of a cluster combination-based sort protocol that may be used by a resonance inspection tool, and that requires a user to select a single fixed first cluster combination array of the type shown in FIG. 13A.

Another embodiment of what may be characterized as a cluster-based sort protocol for classifying a part 202 (e.g., assigning the part 202 to a first classification 210; assigning the part 202 to a second classification 212) is presented in FIG. 15, is identified by reference numeral 350, and may be executed by any appropriate resonance inspection tool (e.g., resonance inspection tool 100 of FIG. 3; resonance inspection tool 100' of FIG. 6, where the cluster-based sort logic 214 may be configured in accordance with the sort protocol 350). Step 354 of the sort protocol 350 is directed to loading, selecting, or identifying a particular first cluster array 320, while step 356 is directed to loading, selecting, or identifying a particular second cluster array 330. Steps 354 and 356 may be executed in any appropriate order. It should be appreciated that a particular resonance inspection tool may be preconfigured with a particular first cluster array 320 and a particular second cluster array 330. It should also be appreciated that a given first cluster array 320 could be associated with a particular second cluster array 330, and vice versa. Therefore, selecting a particular first cluster array 320 (step 354; e.g., from a plurality of first cluster arrays 320) could result in the resonance inspection tool automatically selecting the corresponding second cluster array 330 (step 356; e.g., from a plurality of second cluster arrays 330). Similarly, selecting a particular second cluster array 330 (step 356; e.g., from a plurality of second cluster arrays 330) could result in the resonance inspection tool automatically selecting the corresponding first cluster array 320 (step 354; e.g., from a plurality of first cluster arrays 320).

Step 358 of the sort protocol 350 of FIG. 15 is directed to loading, selecting, or identifying a particular first cluster 322 within the first cluster array 320 (step 354), and which is based upon user input. The first cluster array 320 again includes a plurality of first clusters 322. This selection (step 358) may be done in any appropriate manner, including through an appropriate user interface for the resonance inspection tool. For instance, the various first clusters 322 of the first cluster array 320 could be listed on an appropriate display (e.g., in a drop-down menu), and a user could select the desired first cluster 322 from this listing. Another option would be for a user to enter one or more search terms and which may be used to display one or more first clusters 322 of the first cluster array 320 that satisfy the search term(s). A user could then select one of the first clusters 322 in the noted manner. In any case, the particular first cluster 322 of the first cluster array 320 that is thereafter to be used by the sort protocol 350 will be referred to a "target first cluster 322."

The "user input" for purposes of step 358 of the sort protocol 350 of FIG. 15 could be the above-noted "cluster selection data 218." Exemplary cluster selection data 218 includes manufacturer data, manufacturing data, specified component data, and specified service-related data, individually and in each combination. As such, the target first cluster 322 for purposes of the sort protocol 350 of FIG. 15 may be a particular one of the first clusters 322 from the first cluster array 320, where this first cluster 322 from the first cluster array 220 includes a plurality of parts that are each of the first classification 210, that each have a common resonance data pattern, and furthermore that each comply with all cluster selection data 218 that may be provided pursuant to step 358.

Part data 200 (at least a frequency response or resonance data) is acquired on the part 202 pursuant to step 360 of the sort protocol 350. The part data 200 on the part 202 may be in accordance with the foregoing (e.g., where the part 202 is excited at a plurality of different input frequencies, and where the response of the part 202 at each particular input frequency is incorporated by the frequency response for the part 202 and becomes at least part of the part data 200). In the case where cluster selection data 218 is used by the sort protocol 350, corresponding data on the part 202 may be acquired pursuant to step 360. In any case, the part data 200 is tested against a plurality of sorts 204 of a single fixed first cluster combination array or group 340a in the case of the sort protocol 350 of FIG. 15. This single fixed first cluster combination array or group 340a is defined in the above-noted manner from the target first cluster 322 (358) of the first cluster array 320 (step 354), in combination with each second cluster from the second cluster array 330 (step 356).

The part data 200 (step 360) is tested against the sort 204 for one of the cluster combinations 342 of the fixed first cluster combination array 340a for the target first cluster 322 (step 358) pursuant to each execution of step 362 for the sort protocol 350 of FIG. 15. The various sorts 204 for purposes of this fixed first cluster combination array 340a again may be viewed as simultaneously assessing two different clusters (e.g., the same target first cluster 322 from the first cluster array 320 (first classification 210) and one second cluster 332 from the corresponding second cluster array 330 (second classification 212), shown in FIG. 12). As each sort 204 from the fixed first cluster combination array 340a for the target first cluster 322 at least in effect simultaneously assesses two different clusters (e.g., the same target first cluster 322 (step 358) from the first cluster array 320 and one second cluster 332 from the corresponding second cluster array 330 of FIG. 12), a sort 204 for purposes of the fixed first cluster combination array 340a for the target first cluster 322 (step 358, and for use by the sort protocol 350 of FIG. 15) may be characterized as being configured to: 1) provide a discrimination function in relation to clustered parts in one of the first clusters of the first cluster array 320 (corresponding with the target first cluster 322 (step 358)); and 2) also provide a discrimination function in relation to clustered parts in one of the second clusters 332 of the corresponding second cluster array 330. Generally, the sort protocol 350 of FIG. 15 is directed to determining if the part 202 should be assigned to the first classification 210 (e.g., an accepted/acceptable part classification) or to the second classification 212 (e.g., a rejected/unacceptable part classification). With regard to this function and as used herein, the phrase "passing a sort 204" or the like may be associated with this particular sort 204 determining that the part 202 should be assigned to a first classification 210—the results of the sort 204 in this instance may indicate that the part 202 should be assigned to a first classification 210. Conversely, the phrase "failing a sort 204" or the like may be associated with this particular sort 204 determining that the part 202 should be assigned to a different second classification 212—the results of the sort 204 in this instance may indicate that the part 202 should be assigned to a second classification 212.

A given sort 204 for purposes of the sort protocol 350 and the fixed first cluster combination array 340a for the target first cluster 322 (step 358) may be characterized as "passing" in relation to the testing of a certain part 202 against the sort 204: 1) if the predetermined attributes and/or relationships of the clustered parts in the target first cluster 322 of the first cluster array 320 (step 358) exist in the part data 200 on the part 202; and 2) if the part data 200 on the part 202 excludes the predetermined attributes and/or relationships of the clustered parts in the particular second cluster 332 of the corresponding second cluster array 330. Otherwise, the testing of this part 202 (e.g., its part data 200) against the sort 204 may be deemed to have failed the sort 204.

Step 364 of the sort protocol 350 of FIG. 15 is directed toward determining if the part data 200 on the part 202 has been tested against all cluster combinations 342 of the fixed first cluster combination array 340a for the target first cluster 322 (step 358). If not, the cluster combination 342 is updated pursuant to step 366 (e.g., another cluster combination 342/sort 204 is selected), and control is returned to step 362 for repetition in accordance with the foregoing. On the first execution of step 362, the part data 200 on the part 202 may be tested against the sort 204a for the cluster combination 342a of the fixed first cluster combination array 340a for the target first cluster 322 (step 358). As the part data 200 on the part 202 would not have been tested against the sorts 204b-d (FIG. 13A) in this example, the "updated cluster combination 342" for purposes of the first execution of step 366 may be the cluster combination 342b (FIG. 13A), and steps 362 and 364 may be repeated in accordance with the foregoing. This may be repeated in this manner for the entire fixed first cluster combination array 340a for the target first cluster 322 (step 358) (e.g., the sort protocol 350 may sequence through the fixed first cluster combination array 340a for the target first cluster 322 (step 358) in the top-to-down order presented in FIG. 13A and in one-step increments). It should be appreciated that the sort protocol 350 may sequence through the fixed first cluster combination array 340a for the target first cluster 322 (step 358) in any appropriate fashion so long as the part data 200 on the part 202 is eventually tested against each sort 204 of the fixed first cluster combination array 340a for the target first cluster 322 (step 358) (i.e., the sort protocol 350 does not have to test the part data 200 on the part 202 against the sorts 204 in the top-to-down order presented in FIG. 13A, and in one step increments).

Once step 364 of the sort protocol 350 of FIG. 15 determines that the part data 200 on the part 202 has been tested against all sorts 204 of the fixed first cluster combination array 340a for the target first cluster 322 (step 358), control is transferred from step 364 to step 368. Step 368 is directed to determining if the sort results of each sort 204 of the fixed first cluster combination array 340a for the target first cluster 322 (step 358) is equated with a first classification 210. If each sort 204 of the fixed first cluster combination array 340a for the target first cluster 322 (step 358) provided a first classification 210 sort result, the sort protocol 350 proceeds from step 368 to step 370 where the part 202 is assigned a first classification 210. Otherwise, step 372 of the sort protocol 350 assigns the part 202 a second classification 212.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A method of evaluating a part, comprising the steps of:
   acquiring part data on a first part for a resonance inspection tool, wherein said part data comprises a frequency response of said first part, wherein said resonance inspection tool comprises a first cluster array which in turn comprises a plurality of first clusters that are each of a first classification, wherein each first cluster of said plurality of first clusters is also associated with a different resonance data pattern, wherein said resonance inspection tool further comprises a second cluster array which in turn comprises a plurality of second clusters that are each of a second classification, wherein each second cluster of said plurality of second clusters is also associated with a different resonance data pattern, wherein said first classification is an accepted part classification, wherein said second classification is a rejected part classification, wherein a fixed first cluster combination array comprises a plurality of cluster combinations defined by a common said first cluster from said first cluster array and each said second cluster from said second cluster array, and wherein each said cluster combination of a given said fixed first cluster combination array has a dedicated sort;
   testing said part data against said sort for each cluster combination from a current said fixed first cluster combination array;
   executing a first assigning step comprising assigning said first part to said first classification if said sort for each said cluster combination of the current said fixed first cluster combination array from said testing step provides a first classification sort result;
   updating the current said fixed first cluster combination array if said first assigning step fails to be executed and if there is another said fixed first cluster combination array that is definable from said first cluster array and said second cluster array;
   repeating said testing step and assessing for execution of said first assigning step for each execution of said updating step; and
   executing a second assigning step when said first assigning step fails to be executed for each said fixed first cluster combination array that definable from said first cluster array and said second cluster array, wherein said second assigning step comprises assigning said first part to said second classification;
   wherein said testing step, said first assigning step, said updating step, said assessing step, and said second assigning step are each executed by said resonance inspection tool.

2. The method of claim 1, wherein said acquiring part data step comprises exciting said first part at a plurality of input frequencies and that is defined by said plurality of input frequencies.

3. The method of claim 1, wherein each said first cluster comprises a plurality of first clustered parts that are each of said first classification, and wherein each said second cluster comprises a plurality of second clustered parts that are each of said second classification.

4. The method of claim 3, wherein each first clustered part of said plurality of first clustered parts for each said first cluster comprises a non-defective part, wherein each second clustered part of said plurality of second clustered parts for each said second cluster comprises a defective part, wherein there is a different acceptance basis for each said first cluster, and wherein there is a different rejection basis for each said second cluster.

5. The method of claim 4, wherein each said first clustered part in each said first cluster comprises a common acceptance basis, and wherein each said second clustered part in each said second cluster comprises a common rejection basis.

6. The method of claim 5, wherein each said rejection basis comprises at least one of defect type and defect location.

7. The method of claim 1, wherein said plurality of first clusters are clustered based upon at least one first clustering parameter in addition to said first classification and their corresponding said resonance data pattern, and wherein said plurality of second clusters are clustered based upon at least one second clustering parameter in addition to said second classification and their corresponding said resonance data pattern.

8. The method of claim 7, wherein clustering of said plurality of second clusters is done without regard to said at least one first clustering parameter.

9. The method of claim 1, wherein each said first cluster of said plurality of first clusters comprises a plurality of first clustered parts, and wherein each first clustered part of said plurality of first clustered parts in the same said first cluster has a common said resonance data pattern and is further associated with at least one of:
- a common manufacturer;
- common first specified component data;
- common first specified manufacturing data; and
- common first specified service-related data.

10. The method of claim 9, further comprising:
receiving cluster selection data; and
defining said first cluster array from said cluster selection data, wherein said receiving and defining steps are executed by said resonance inspection tool, and wherein said cluster selection data is selected from the group consisting of manufacturer data, manufacturing data, component data, service-related data, and any combination thereof.

11. The method of claim 9, wherein each said second cluster of said plurality of second clusters comprises a plurality of second clustered parts, and wherein each second clustered part of said plurality of second clustered parts in the same said second cluster has a common said resonance data pattern and is further associated with at least one of:
- a common manufacturer;
- common second specified component data;
- common second specified manufacturing data; and
- common second specified service-related data.

12. The method of claim 1, further comprising:
receiving cluster selection data; and
defining said first cluster array from said cluster selection data, wherein said receiving and defining steps are executed by said resonance inspection tool, and wherein said cluster selection data is selected from the group consisting of manufacturer data, manufacturing data, component data, service-related data, and any combination thereof.

13. The method of claim 1, wherein each said second cluster of said plurality of second clusters comprises a plurality of second clustered parts, and wherein each second clustered part of said plurality of second clustered parts in the same said second cluster has a common said resonance data pattern and is further associated with at least one of:
- a common manufacturer;
- common specified component data;
- common specified manufacturing data; and
- common specified service-related data.

14. A method of evaluating a part, comprising the steps of:
acquiring part data on a first part for a resonance inspection tool, wherein said part data comprises a frequency response of said first part, wherein said resonance inspection tool comprises a first cluster array which in turn comprises a plurality of first clusters that are each of a first classification, wherein each first cluster of said plurality of first clusters is also associated with a different resonance data pattern, wherein said resonance inspection tool further comprises a second cluster array which in turn comprises a plurality of second clusters that are each of a second classification, wherein each second cluster of said plurality of second is also associated with a different resonance data pattern, wherein said first classification is an accepted part classification, wherein said second classification is a rejected part classification, wherein a fixed second cluster combination array comprises a plurality of cluster combinations defined by a common said second cluster from said second cluster array and each said first cluster from said first cluster array, and wherein each said cluster combination of a given said fixed second cluster combination array has a dedicated sort;

testing said part data against said sort for each cluster combination from a current said fixed second cluster combination array;
executing a first assigning step comprising assigning said first part to said first classification if said sort for at least one said cluster combination of the current said fixed second cluster combination array from said testing step provides a first classification sort result;
updating the current said fixed second cluster combination array if said first assigning step fails to be executed and if there is another said fixed second cluster combination array that is definable from said first cluster array and said second cluster array;
repeating said testing step and assessing for execution of said first assigning step for each execution of said updating step; and
executing a second assigning step when said first assigning step fails to be executed for each said fixed second cluster combination array that definable from said first cluster array and said second cluster array, and wherein said second assigning step comprises assigning said first part to said second classification;
wherein said testing step, said first assigning step, said updating step, said assessing step, and said second assigning step are each executed by said resonance inspection tool.

15. The method of claim 14, wherein said acquiring part data step comprises exciting said first part at a plurality of input frequencies and that is defined by said plurality of input frequencies.

16. The method of claim 14, wherein each said first cluster comprises a plurality of first clustered parts that are each of said first classification, and wherein each said second cluster comprises a plurality of second clustered parts that are each of said second classification.

17. The method of claim 16, wherein each first clustered part of said plurality of first clustered parts for each said first cluster comprises a non-defective part, wherein each second clustered part of said plurality of second clustered parts for each said second cluster comprises a defective part, wherein there is a different acceptance basis for each said first cluster, and wherein there is a different rejection basis for each said second cluster.

18. The method of claim 17, wherein each said first clustered part in each said first cluster comprises a common acceptance basis, and wherein each said second clustered part in each said second cluster comprises a common rejection basis.

19. The method of claim 18, wherein each said rejection basis comprises at least one of defect type and defect location.

20. The method of claim 14, wherein said plurality of first clusters are clustered based upon at least one first clustering parameter in addition to said first classification and their corresponding said resonance data pattern, and wherein said plurality of second clusters are clustered based upon at least one second clustering parameter in addition to said second classification and their corresponding said resonance data pattern.

21. The method of claim 20, wherein clustering of said plurality of second clusters is done without regard to said at least one first clustering parameter.

22. The method of claim 14, wherein each said first cluster of said plurality of first clusters comprises a plurality of first clustered parts, and wherein each first clustered part of said plurality of first clustered parts in the same said first cluster has a common said resonance data pattern and is further associated with at least one of:
- a common manufacturer;
- common first specified component data;
- common first specified manufacturing data; and
- common first specified service-related data.

23. The method of claim 22, further comprising:
receiving cluster selection data; and
defining said first cluster array from said cluster selection data, wherein said receiving and defining steps are executed by said resonance inspection tool, and wherein said cluster selection data is selected from the group consisting of manufacturer data, manufacturing data, component data, service-related data, and any combination thereof.

24. The method of claim 22, wherein each said second cluster of said plurality of second clusters comprises a plurality of second clustered parts, and wherein each second clustered part of said plurality of second clustered parts in the same said second cluster has a common said resonance data pattern and is further associated with at least one of:
- a common manufacturer;
- common second specified component data;
- common second specified manufacturing data; and
- common second specified service-related data.

25. The method of claim 14, further comprising:
receiving cluster selection data; and
defining said first cluster array from said cluster selection data, wherein said receiving and defining steps are executed by said resonance inspection tool, and wherein said cluster selection data is selected from the group consisting of manufacturer data, manufacturing data, component data, service-related data, and any combination thereof.

26. The method of claim 14, wherein each said second cluster of said plurality of second clusters comprises a plurality of second clustered parts, and wherein each second clustered part of said plurality of second clustered parts in the same said second cluster has a common said resonance data pattern and is further associated with at least one of:
- a common manufacturer;
- common specified component data;
- common specified manufacturing data; and
- common specified service-related data.

27. A method of evaluating a part, comprising the steps of:
receiving a selection of a single first cluster from a first cluster array that comprises a plurality of first clusters that are each of a first classification, wherein a resonance inspection tool comprises said first cluster array, wherein said receiving a selection step is based upon user input, wherein a second cluster array comprises a plurality of second clusters that are each of a second classification, wherein said resonance inspection tool further comprises said second cluster array, wherein said first classification is an accepted part classification, wherein each first cluster of said plurality of first clusters is also associated with a different resonance data pattern, wherein said second classification is a rejected part classification, wherein each second cluster of said plurality of second clusters is associated with a different resonance data pattern, wherein a fixed first cluster combination array comprises a plurality of cluster combinations defined by said selection of said single first cluster from said first cluster array and each said second cluster from said second cluster array, and wherein each said cluster combination of said fixed first cluster combination array has a dedicated sort;

acquiring part data on a first part for a resonance inspection tool, wherein said part data comprises a frequency response of said first part;

testing said part data against said sort for each cluster combination from said fixed first cluster combination array;

executing a first assigning step comprising assigning said first part to said first classification if said sort for each said cluster combination of said fixed first cluster combination array from said testing step provides a first classification sort result; and executing a second assigning step comprising assigning said first part to said second classification if said sort for at least one said cluster combination of said fixed first cluster combination array from said testing step provides a second classification sort result;

wherein said selecting step, said testing step, said first assigning step, and said second assigning step are each executed by said resonance inspection tool.

28. The method of claim 27, wherein said selection is based upon cluster selection data that is input to said resonance inspection tool and is selected from the group consisting of specified manufacturer data, specified manufacturing data, specified component data, specified service-related data, and any combination thereof.

* * * * *